(12) United States Patent
Nagai et al.

(10) Patent No.: US 6,846,607 B2
(45) Date of Patent: Jan. 25, 2005

(54) CARBAZOLE DERIVATIVE AND CHEMICALLY AMPLIFIED RADIATION-SENSITIVE RESIN COMPOSITION

(75) Inventors: Tomoki Nagai, Mie (JP); Jun Numata, Mie (JP); Shirou Kusumoto, Austin, TX (US); Eiichi Kobayashi, Mie (JP)

(73) Assignee: JSR Corporation, Tokyo (JP)

( * ) Notice: Subject to any disclaimer, the term of this patent is extended or adjusted under 35 U.S.C. 154(b) by 96 days.

(21) Appl. No.: 10/087,735

(22) Filed: Mar. 5, 2002

(65) Prior Publication Data

US 2002/0172885 A1 Nov. 21, 2002

(30) Foreign Application Priority Data

Mar. 6, 2001 (JP) ........................................ 2001/061922

(51) Int. Cl.$^7$ .......................... G03F 7/004; G03F 7/30; C07D 209/86
(52) U.S. Cl. .................... 430/170; 430/270.1; 430/905; 430/910; 548/445
(58) Field of Search .............................. 430/170, 270.1, 430/905, 910; 548/445

(56) References Cited

U.S. PATENT DOCUMENTS 6,004,719 A    12/1999    Gaudiana et al.
6,177,240 B1 *   1/2001    Yamada et al. ............. 430/619

FOREIGN PATENT DOCUMENTS

JP       57212457 A   * 12/1982            G03G/5/08

OTHER PUBLICATIONS

Conn, M.M., et al., "Convergent Functional Groups. 13. High–Affinity Complexation Of Adenosine Derivatives Within Induced Binding Pockets", J. Am. Chem. Soc., 115: 3548–57 (1993).
Shukla, Y. K. , "Synthesis Of Some New Aryl α–(3–Substituted–Carbazol–9–YL) Acetates/Propionates As Possible Antiinflammatory And Analgesic Agents", Indian J. Chem., 33B: 799–802 (1994).
Mannschreck, Von Albrecht, et al., "Nachweis Diastereomerer Elektronen–Donor–Acceptor–Assoziate Durch $^1$H–NMR–Spektroskopie", Angew. Chem., 90: NR. 12, 995–97 (1978).
Lao, W., et al., "Microwave–Induced Fast Synthesis And Optical Resolution Of 9H–Carbazole–2–Carboxylic Acids Enantiomers", J. Prakt. Chem., 342: 6, 596–8 (2000).
Perié, K., et al., "Novel Electro–Oxidizable Chiral N–Substituted Dicarbazoles And Resulting Electroactive Films For Covalent Attachment Of Proteins", Tetrahedron Letters, 41: 3725–29 (2000).
Okada, Keiji, et al., "A New And Practical Method Of Decarboxylation: Photosensitized Decarboxylation Of N–Acyloxyphthalimides Via Electron–Transfer Mechanism", J. Am. Chem. Soc., 110: 8736–38 (1988).

* cited by examiner

Primary Examiner—John S. Chu
(74) Attorney, Agent, or Firm—Piper Rudnick LLP; Steven B. Kelber

(57) ABSTRACT

A carbazole derivative of the following formula (1),

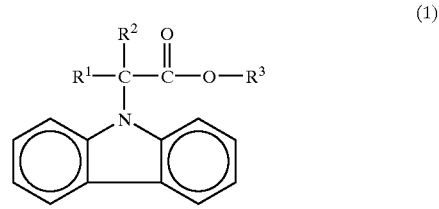

wherein $R^1$ and $R^2$ individually represent a hydrogen atom or a monovalent organic group, or $R^1$ and $R^2$ form, together with the carbon atom to which $R^1$ and $R^2$ bond, a divalent organic group having a 3–8 member carbocyclic structure or a 3–8 member heterocyclic structure, and $R^3$ represents a hydrogen atom or a monovalent organic group. The carbazole derivative is suitable as an additive for increasing sensitivity of a chemically amplified resist. A chemically amplified radiation-sensitive resin composition, useful as a chemically amplified resist, comprising the carbazole derivative is also disclosed.

22 Claims, 3 Drawing Sheets

CARBAZOLE DERIVATIVE AND CHEMICALLY AMPLIFIED RADIATION-SENSITIVE RESIN COMPOSITION

BACKGROUND OF THE INVENTION

1. Field of the Invention

The present invention relates to a novel carbazole derivative and a chemically amplified radiation-sensitive resin composition comprising the carbazole derivative suitable as a chemically-amplified resist useful for microfabrication utilizing various types of radiation represented by deep ultraviolet rays such as a KrF excimer laser, ArF excimer laser, EUV, or $F_2$ excimer laser, X-rays such as synchrotron radiation, or charged particle rays such as electron beams.

2. Description of the Background Art

In the field of microfabrication represented by fabrication of integrated circuit devices, lithographic technology enabling microfabrication with a line width of 0.20 μm or less is demanded in recent years in order to achieve a higher degree of integration.

A conventional lithographic process utilizes near ultraviolet rays such as an i-line radiation. It is known in the art that microfabrication with a line width of a sub-quarter micron order using near ultraviolet rays is very difficult.

Therefore, use of radiation with a shorter wavelength has been studied for enabling microfabrication with a line width of 0.20 μm or less. As radiation with a shorter wavelength, deep ultraviolet rays represented by a line spectrum of a mercury lamp and an excimer laser, X-rays, electron beams, and the like can be given. Of these, a KrF excimer laser (wavelength: 248 nm), an ArF excimer laser (wavelength: 193 nm), and an $F_2$ excimer laser (wavelength: 157 nm) have attracted attention.

As a resist applicable to the shorter wavelength radiations, a number of resists utilizing a chemical amplification effect between a component having an acid-dissociable functional group and a photoacid generator which generates an acid upon irradiation (hereinafter called "exposure") has been proposed. Such a resist is hereinafter called a chemically amplified resist.

As a chemically amplified resist, Japanese Patent Publication No. 27660/1990 discloses a composition comprising a polymer having a t-butyl ester group of a carboxylic acid or t-butylcarbonate group of phenol and a photoacid generator. This composition utilizes the effect of the polymer to release a t-butyl ester group or t-butyl carbonate group by the action of an acid generated upon exposure to form an acidic functional group such as a carboxylic group or a phenolic hydroxyl group, which renders an exposed area on a resist film readily soluble in an alkaline developer.

In recent years, in addition to high limit resolution and high process margin, a high sensitivity to radiations is demanded of chemically amplified resists as a factor determining productivity of a photolithographic process.

Reducing the amount of basic substance which is a component of chemically amplified resists is one of the methods of increasing the sensitivity of the chemically amplified resists. This method, however, not only involves a decrease in the amount of acids produced by a photoacid generator, which gives rise to unduly roughened pattern surfaces, but also impairs environmental resistance of the resist such as poor PED stability, which is an indication of line width stability against a fluctuated period of time from exposure to post heat treatment. One method for obviating this problem is to increase the amount of photoacid generator. However, an increased amount of photoacid generator decreases radiation transmissivity through resist films, resulting in a trapezoid pattern profile rather than a desirable rectangular pattern profile.

In an effort of increasing sensitivity by the use of additives, Japanese Patent Application Laid-open No. 34272/2000 discloses a method of adding a cyclic 1,2-diolmonosulfonate compound as an agent to assist acid generation. However, this method may affect storage stability of radiation-sensitive resin compositions. When the photoacid generator is accidentally decomposed for some reason, an acid may be rapidly produced due to the action of the acid generation assisting agent.

The effect of carbazole compounds to increase the sensitivity of succinimide esters used as a photoacid generator has been reported (J. Am. Chem. Soc. 1988, 110, 8736). However, this type of compound is highly toxic and readily sublimable. The compound may splash when forming resist patterns, soils the exposure apparatus, and may have an adverse effect on human bodies.

Accordingly, development of a non-sublimable resist additive capable of increasing sensitivity without affecting basic photo-resist performance such as high resolution and pattern profile, and providing a chemically amplified radiation-sensitive resin composition possessing high environmental resistance and storage stability is strongly desired.

Therefore, an object of the present invention is to provide a novel carbazole derivative which is very useful as a component for increasing sensitivity of a chemically amplified resist having sensitivity to radiation such as deep ultraviolet rays represented by a KrF excimer laser, ArF excimer laser, and $F_2$ excimer laser, and a radiation-sensitive resin composition comprising such a carbazole derivative exhibiting superior sensitivity as a resist without affecting basic resist performance such as resolution, pattern profile, and stability to resist fluctuations of the period of time from exposure to post heat treatment, and suitably used as a chemically amplified resist possessing excellent environmental resistance and storage stability.

SUMMARY OF THE INVENTION

The above object can be solved in the present invention by a carbazole derivative of the following formula (1),

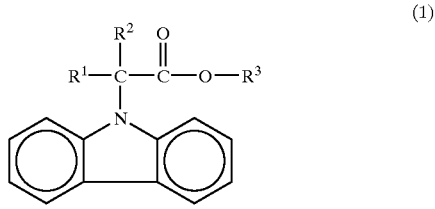

(1)

wherein $R^1$ and $R^2$ individually represent a hydrogen atom or a monovalent organic group, or $R^1$ and $R^2$ form, together with the carbon atom to which $R^1$ and $R^2$ bond, a divalent organic group having a 3–8 member carbocyclic structure or a 3–8 member heterocyclic structure, and $R^3$ represents a hydrogen atom or a monovalent organic group.

The above object can be further solved in the present invention by a chemically amplified radiation-sensitive resin composition comprising the carbazole derivative of the above formula (1).

Other objects, features and advantages of the invention will hereinafter become more readily apparent from the following description.

DETAILED DESCRIPTION OF THE INVENTION AND PREFERRED EMBODIMENTS

Figure 1:
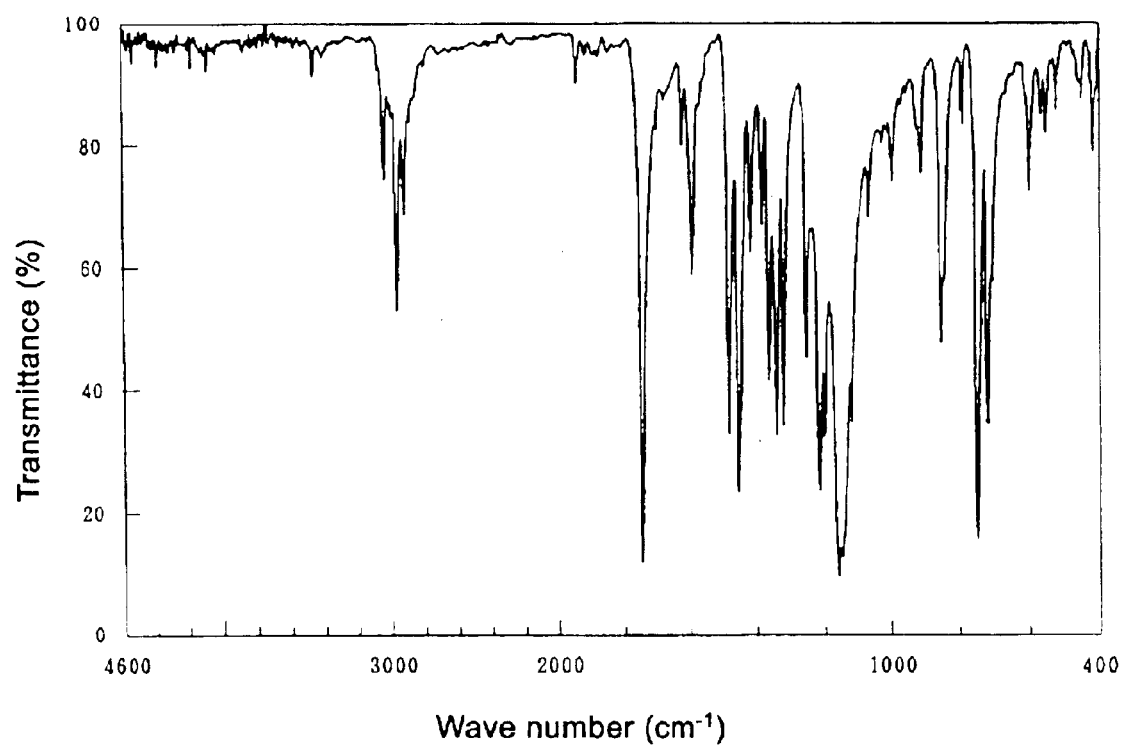
FIG. 1 is an IR absorption spectrum of the carbazole derivative (1) prepared in Synthetic Example 2.

The present invention will be described in detail below.

Carbazole Derivative (1)

The carbazole derivative of the present invention, represented by the above formula (1) (hereinafter referred to as "carbazole derivative (1)"), possesses a carbazole skeleton, which is a chromophore or light-absorbing site in the molecule, and exhibits the effect of sensitizing photoacid generators such as an onium salt, sulfonimide, and disulfonyl diazomethane. This compound does not sublimate because of the non-plane structure due to bonding of the carboxylic ester moiety via a carbon atom with an Sp$^3$ orbit.

As examples of the monovalent organic group represented by $R^1$ and $R^2$ in the carbazole derivative (1), linear, branched, or cyclic alkyl groups having 1–12 carbon atoms, aromatic hydrocarbon groups having 6–20 carbon atoms, oxygen-containing organic groups, and nitrogen-containing organic groups can be given.

As examples of the alkyl groups, a methyl group, ethyl group, n-propyl group, i-propyl group, n-butyl group, 2-methylpropyl group, 1-methylpropyl group, t-butyl group, cyclopentyl group, and cyclohexyl group can be given. As examples of the aromatic hydrocarbon groups, a phenyl group, o-tolyl group, m-tolyl group, p-tolyl group, 2,4-xylyl group, 2,6-xylyl group, 3,5-xylyl group, mesityl group, o-cumenyl group, m-cumenyl group, p-cumenyl group, benzyl group, phenethyl group, 1-naphthyl group, and 2-naphthyl group can be given.

The following groups can be given as examples of the oxygen-containing organic groups: a carboxyl group; linear, branched, or cyclic hydroxyalkyl groups having 1–8 carbon atoms such as a 1-hydroxymethyl group, 1-hydroxyethyl group, 2-hydroxyethyl group, 1-hydroxypropyl group, 2-hydroxypropyl group, 3-hydroxypropyl group, 1-hydroxybutyl group, 2-hydroxybutyl group, 3-hydroxybutyl group, 4-hydroxybutyl group, 3-hydroxycyclopentyl group, and 4-hydroxycyclohexyl group; linear, branched, or cyclic alkoxyl groups having 1–8 carbon atoms such as a methoxy group, ethoxy group, n-propoxy group, i-propoxy group, n-butoxy group, 2-methylpropoxy group, 1-methylpropoxy group, t-butoxygroup, cyclopentyloxy group, and cyclohexyloxy group; linear, branched, or cyclic alkoxyalkyl groups having 2-10 carbon atoms such as a methoxymethyl group, ethoxymethyl group, n-propoxymethyl group, i-propoxymethyl group, n-butoxymethyl group, t-butoxymethyl group, cyclopentyloxymethyl group, and cyclohexyloxymethyl group; linear or branched 1-alkoxyalkoxy groups having 2–10 carbon atoms such as a 1-methoxyethoxy group, 1-ethoxyethoxy group, 1-n-propoxyethoxy group, 1-n-butoxyethoxy group, 1-cyclopentyloxyethoxy group, 1-cyclohexyloxyethoxy group, 1-methoxypropoxy group, 1-ethoxypropoxy group, 1-cyclopentyloxyethoxy group, and 1-cyclohexyloxyethoxy group; linear, branched, or cyclic alkoxycarbonyloxy groups having 2-9 carbon atoms such as a methoxycarbonyloxy group, ethoxycarbonyl oxy group, n-propoxycarbonyloxy group, i-propoxycarbonyloxy group, n-butoxycarbonyloxy group, t-butoxycarbonyloxy group, cyclopentyloxycarbonyloxy group, and cyclohexyloxy carbonyloxy group; linear or branched (1-alkoxyalkoxy)alkyl groups having 3–11 carbon atoms such as a (1-methoxyethoxy)methyl group, (1-ethoxyethoxy)methyl group, (1-n-propoxyethoxy)methyl group, (1-n-butoxyethoxy)methyl group, (1-cyclopentyloxyethoxy)methyl group, (1-cyclohexyloxyethoxy)methyl group, (1-methoxypropoxy)methyl group, and (1-ethoxypropoxy) methyl group; linear, branched, or cyclic alkoxycarbonyloxyalkyl groups having 3–10 carbon atoms such as a methoxycarbonyloxymethyl group, ethoxycarbonyloxymethyl group, n-propoxycarbonyloxymethyl group, i-propoxycarbonyloxymethyl group, n-butoxycarbonyloxymethyl group, t-butoxycarbonyloxymethyl group, cyclopentyloxycarbonyloxymethyl group, and cyclohexyloxycarbonyloxymethyl group; a tetrahydrofuranyloxy group, tetrahydropyranyloxy group, tetrahydrofuranyloxymethyl group, tetrahydropyranyloxymethyl group, and the like.

Examples of the nitrogen-containing organic groups include a cyano: group; linear, branched, or cyclic cyanoalkyl groups having 2-9 carbon atoms such as a cyanomethyl group, 1-cyanoethyl group, 2-cyanoethyl group, 1-cyanopropyl group, 2-cyanopropyl group, 3-cyanopropyl group, 1-cyanobutyl group, 2-cyanobutyl group, 3-cyanobutyl group, 4-cyanobutyl group, 3-cyanocyclopentyl group, and 4-cyanocyclohexyl group; and the like.

As examples of the divalent organic group having a 3–8 member carbocyclic structure formed by $R^1$, $R^2$, and the carbon atom to which the groups $R^1$ and $R^2$ bond, groups derived from a cyclopropane, cyclobutane, cyclopentane, cyclohexane, cyclohexene, or cyclooctane can be given.

As examples of the divalent organic group having a 3–8 member carbocyclic structure formed by $R^1$, $R^2$, and the carbon atom to which the groups $R^1$ and $R^2$ bond, groups derived from a tetrahydrofuran, tetrahydropyran, 1,4-dioxane, tetrahydrothiofuran, and tetrahydrothiopyran can be given.

As the groups $R^1$ and $R^2$ in the carbazole derivative, a hydrogen atom, methyl group, ethyl group, n-propyl group, i-propyl group, n-butyl group, 2-mehylpropyl group, 1-methylpropyl group, t-butyl group, phenyl group, and benzyl group are preferable. As the divalent organic group having an alicyclic ring formed by $R^1$, $R^2$, and the carbon atom to which $R^1$ and $R^2$ bond, groups derived from a cyclohexane or the like are preferable.

As examples of the monovalent organic group represented by $R^3$, linear, branched, or cyclic alkyl groups having 1–12 carbon atoms, aromatic hydrocarbon groups having 6–20 carbon atoms, oxygen-containing organic groups, nitrogen-containing organic groups, and acid-dissociable organic groups can be given.

As examples of the linear, branched, or cyclic alkyl groups having 1–12 carbon atoms, aromatic hydrocarbon groups having 6–20 carbon atoms, oxygen-containing organic groups, and nitrogen-containing organic groups represented by $R^3$, the corresponding groups given as examples of $R^1$ and $R^2$ can be given. Of these groups, i-propyl group, 1-methylpropyl group, t-butyl group, cyclic alkyl group, benzyl group, cyclic hydroxyalkyl group, alkoxymethyl group, (1-alkoxyalkoxy)methyl group, alkoxycarbonyloxymethyl group, tetrahydrofuranyloxymethyl group, tetrahydropyranyloxymethyl group, and cyclic cyanoalkyl group are included in the acid-dissociable organic groups.

As examples of other acid-dissociable organic groups represented by $R^3$, a substituted methyl group, 1-substituted ethyl group, 1-branched alkyl group, silyl group, germyl group, alkoxycarbonyl group, acyl group, and cyclic acid-dissociable group can be given.

As examples of the above substituted methyl group, a methylthiomethyl group, ethylthiomethyl group, benzyloxymethyl group, benzylthiomethyl group, phenacyl group, bromophenacyl group, methoxyphenacyl group, methylthiophenacyl group, α-methylphenacyl group, cyclopropylmethyl group, diphenylmethyl group, triphenylmethyl group, bromobenzyl group, nitrobenzyl group, methoxybenzyl group, methylthiobenzyl group, ethoxybenzyl group, ethylthiobenzyl group, and piperonyl group can be given.

As examples of the 1-substituted methyl groups, a 1-methoxyethyl group, 1-methylthioethyl group, 1,1-dimethoxyethyl group, 1-ethoxyethyl group, 1-ethylthioethyl group, 1,1-diethoxyethyl group, 1-ethoxypropyl group, 1-propoxyethyl group, 1-cyclohexyloxyethyl group, 1-phenoxyethyl group, 1-phenylthioethyl group, 1,1-diphenoxyethyl group, 1-benzyloxyethyl group, 1-benzylthioethyl group, 1-cyclopropylethyl group, 1-phenylethyl group, 1,1-diphenylethyl group, 1-methoxycarbonylethyl group, 1-ethoxycarbonylethyl group, 1-n-propoxycarbonylethyl group, 1-i-propoxycarbonylethyl group, 1-n-butoxycarbonylethyl group, and 1-t-butoxycarbonylethyl group can be given.

As examples of the 1-branched alkyl groups, a 1,1-dimethylpropyl group, 1-methylbutyl group, and 1,1-dimethylbutyl group can be given.

As examples of the silyl groups, tricarbylsilyl groups such as a trimethylsilyl group, ethyldimethylsilyl group, methyldiethylsilyl group, triethylsilyl group, i-propyldimethylsilyl group, methyldi-1-propylsilyl group, tri-1-propylsilyl group, t-butyldimethylsilyl group, methyldi-t-butylsilyl group, tri-t-butylsilyl group, phenyldimethylsilyl group, methyldiphenylsilyl group, and triphenylsilyl group can be given.

As examples of the germyl groups, tricarbylgermyl groups such as a trimethylgermyl group, ethyldimethylgermyl group, methyldiethylgermyl group, triethylgermyl group, i-propyldimethylgermyl group, methyldi-1-propylgermyl group, tri-1-propylgermyl group, t-butyldimethylgermyl group, methyldi-t-butylgermyl group, tri-t-butylgermyl group, phenyldimethylgermyl group, methyldiphenylgermyl group, and triphenylgermyl group can be given.

As examples of the alkoxycarbonyl group, a methoxycarbonyl group, ethoxycarbonyl group, i-propoxycarbonyl group, and t-butoxycarbonyl group can be given.

As examples of the acyl groups, an acetyl group, propionyl group, butyryl group, heptanoyl group, hexanoyl group, valeryl group, pivaloyl group, isovaleryl group, lauroyl group, myristoyl group, palmitoyl group, stearoyl group, oxalyl group, malonyl group, succinyl group, glutaryl group, adipoyl group, piperoyl group, suberoyl group, azelaoyl group, sebacoyl group, acryloyl group, propioloyl group, methacryloyl group, crotonoyl group, oleoyl group, maleoyl group, fumaroyl group, mesaconoyl group, campholoyl group, benzoyl group, phthaloyl group, isophthaloyl group, terephthaloyl group, naphthoyl group, toluoyl group, hydroatropoyl group, atropoyl group, cinnamoyl group, furoyl group, thenoyl group, nicotinoyl group, isonicotinoyl group, p-toluenesulfonyl group, and mesyl group can be given.

As examples of the cyclic acid-dissociable group, a cyclopropyl group, 3-methylcyclopentyl group, 4-methylcyclohexyl group, cyclohexenyl group, 4-methoxycyclohexyl group, tetrahydrofuranyl group, tetrahydropyranyl group, tetrahydrothiofuranyl group, tetrahydrothiopyranyl group, 3-bromotetrahydropyranyl group, 4-methoxytetrahydropyranyl group, 4-methoxytetrahydrothiopyranyl group, and 3-tetrahydrothiophene-1,1-dioxide can be given.

As the acid-dissociable organic groups represented by $R^3$, an 1-propyl group, 1-methylpropyl group, t-butyl group, cyclohexyl group, benzyl group, t-butoxycarbonylmethyl group, 1-methoxyethyl group, 1-ethoxyethyl group, trimethylsilyl group, t-butoxycarbonyl group, tetrahydrofuranyl group, tetrahydropyranyl group, tetrahydrothiofuranyl group, tetrahydrothiopyranyl group, and the like are preferable.

As the group $R^3$ in the carbazole derivative (1), a hydrogen atom, methyl group, ethyl group, n-propyl group, n-butyl group, 2-methylpropyl group, and phenyl group, as well as the acid-dissociable organic groups such as an i-propyl group, 1-methylpropyl group, t-butyl group, cyclohexyl group, benzyl group, t-butoxycarbonylmethyl group, 1-methoxyethyl group, 1-ethoxyethyl group, trimethylsilyl group, t-butoxycarbonyl group, tetrahydrofuranyl group, tetrahydropyranyl group, tetrahydrothiofuranyl group, tetrahydrothiopyranyl group, and the like are preferable. Of these groups, i-propyl group, t-butyl group, cyclohexyl group, benzyl group, and the like are particularly preferable.

Specific preferable examples of the carbazole derivative (1) include the compounds of the following formulas (1-1) to (1-78).

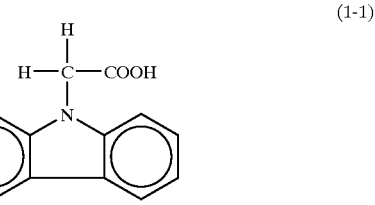

(1-1)

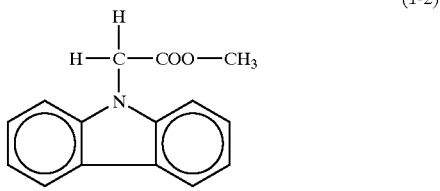

(1-2)

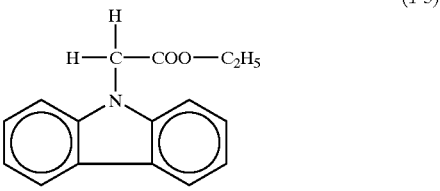

(1-3)

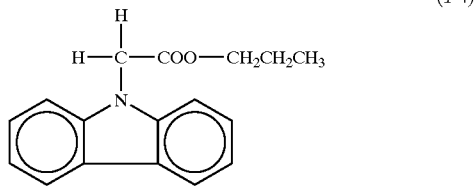

(1-4)

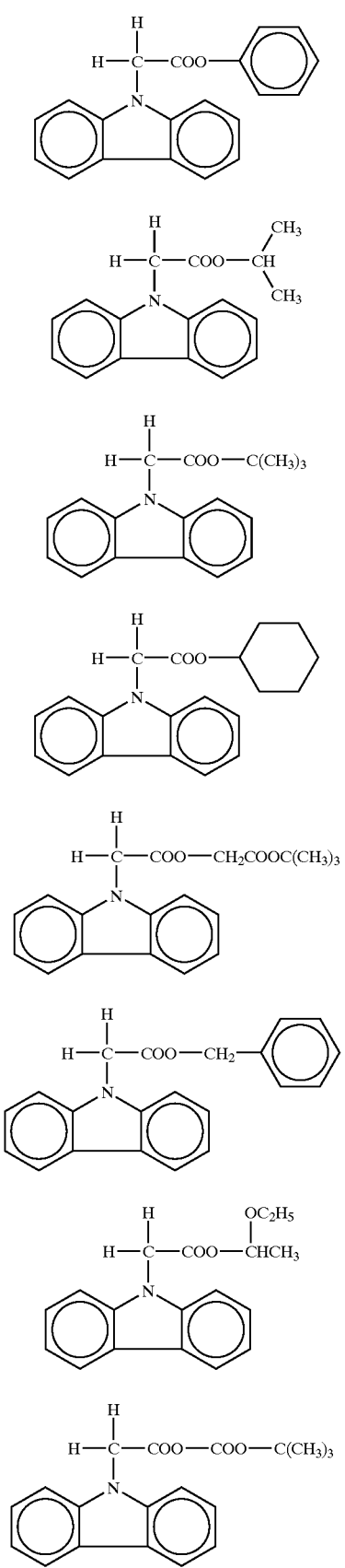
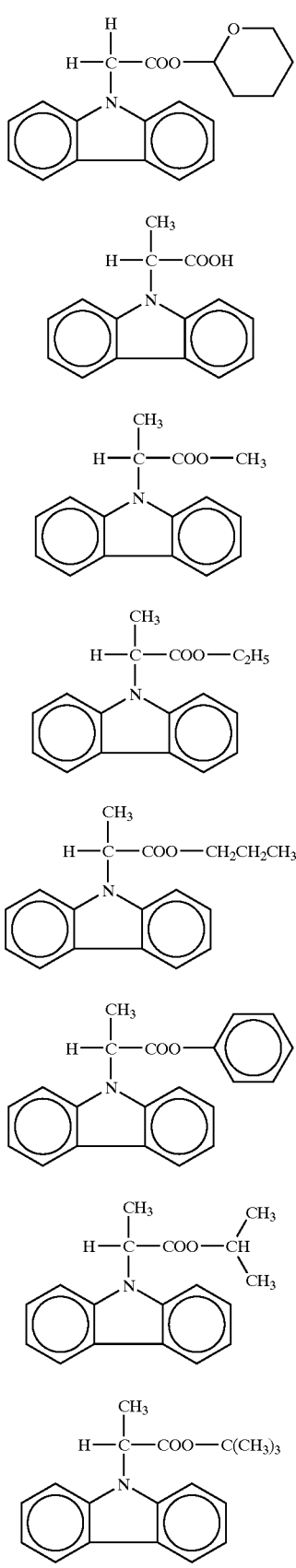

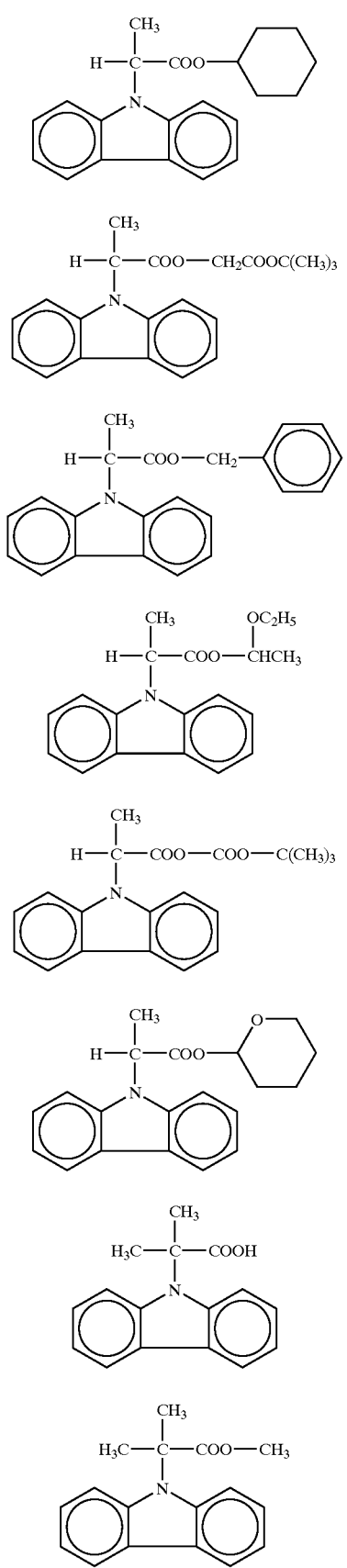
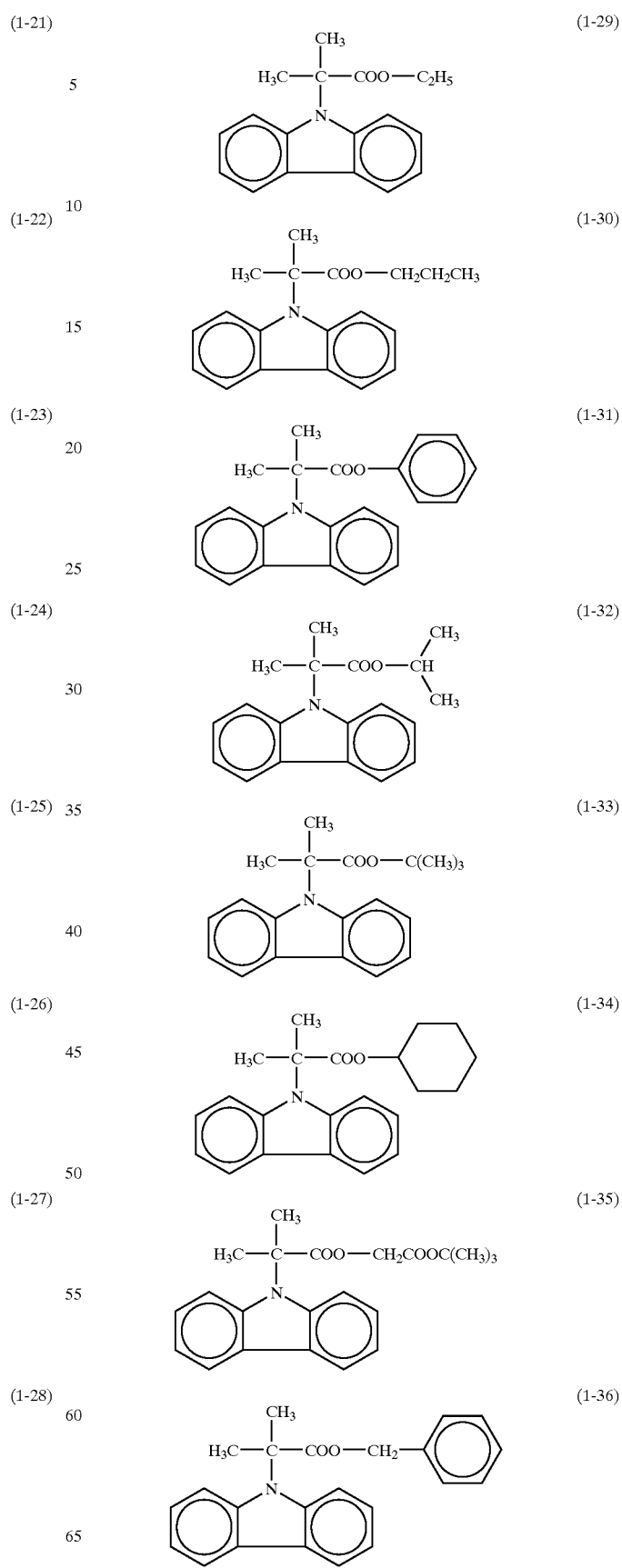

-continued (1-37) Carbazole-N-C(CH₃)₂-COO-CH(CH₃)-OC₂H₅

(1-38) Carbazole-N-C(CH₃)₂-COO-COO-C(CH₃)₃

(1-39) Carbazole-N-C(CH₃)₂-COO-(tetrahydropyran-2-yl)

(1-40) Carbazole-N-CH(C₂H₅)-COOH (1-41) Carbazole-N-CH(C₂H₅)-COO-CH₃

(1-42) Carbazole-N-CH(C₂H₅)-COO-C₂H₅

(1-43) Carbazole-N-CH(C₂H₅)-COO-CH₂CH₂CH₃

(1-44) Carbazole-N-CH(C₂H₅)-COO-C₆H₅

(1-45) Carbazole-N-CH(C₂H₅)-COO-CH(CH₃)₂

(1-46) Carbazole-N-CH(C₂H₅)-COO-C(CH₃)₃

(1-47) Carbazole-N-CH(C₂H₅)-COO-cyclohexyl (1-48) Carbazole-N-CH(C₂H₅)-COO-CH₂COOC(CH₃)₃

(1-49) Carbazole-N-CH(C₂H₅)-COO-CH₂-C₆H₅

(1-50) Carbazole-N-CH(C₂H₅)-COO-CH(CH₃)-OC₂H₅

(1-51) Carbazole-N-CH(C₂H₅)-COO-COO-C(CH₃)₃

(1-52) Carbazole-N-CH(C₂H₅)-COO-(tetrahydropyran-2-yl)

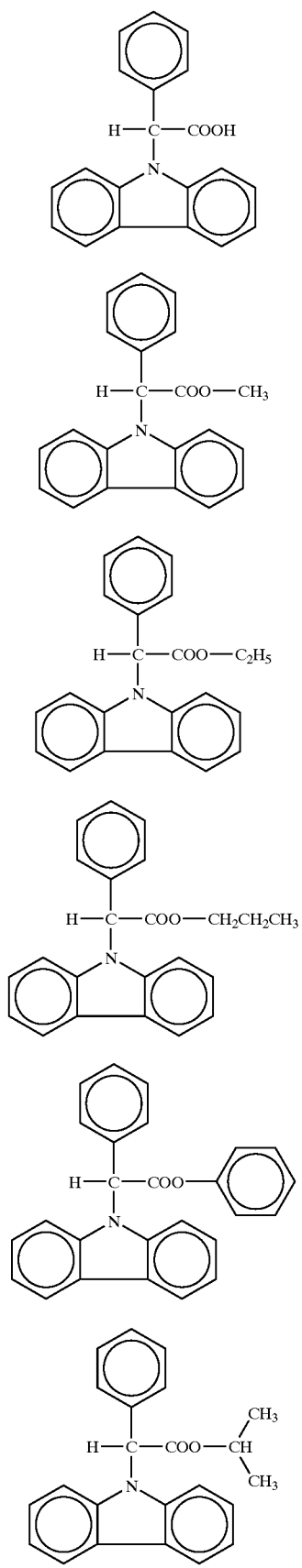
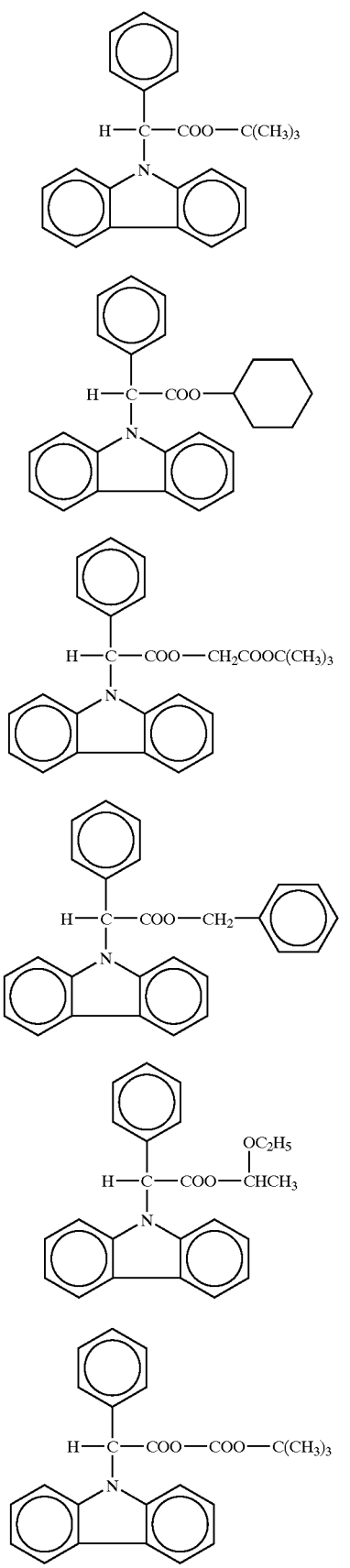

(1-65) 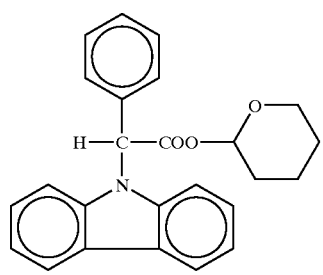
(1-66) 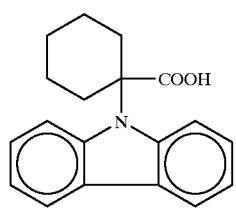
(1-67) 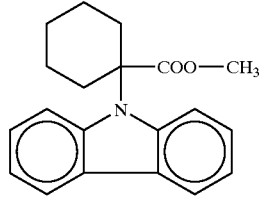
(1-68) 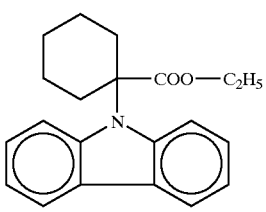
(1-69) 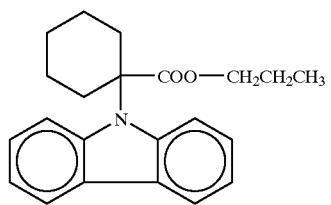
(1-70) 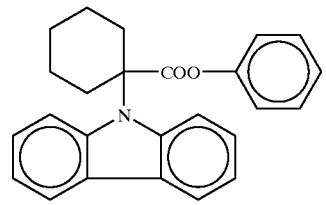
(1-71) 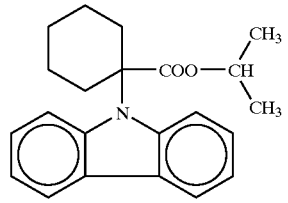
(1-72) 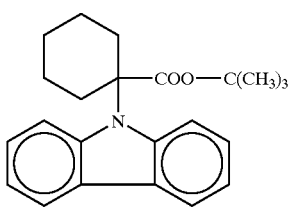
(1-73) 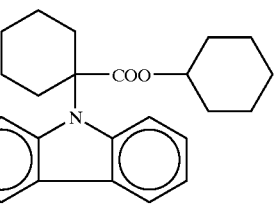
(1-74) 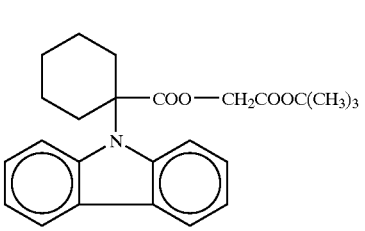
(1-75) 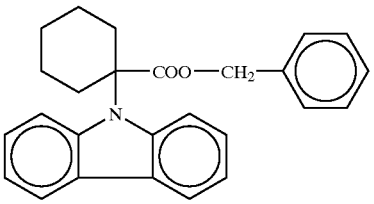
(1-76) 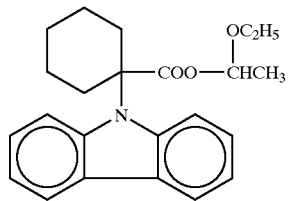
(1-77) 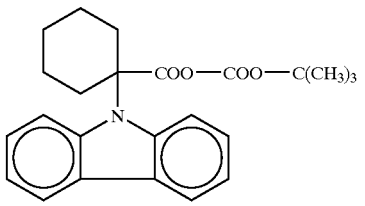
(1--78) 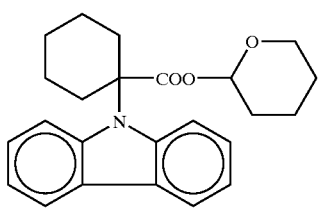

The carbazole derivative (1) can be synthesized by reacting carbazole and an α-bromocarboxylic acid such as bromoacetic acid or an a-bromocarboxylic acid ester such as t-butyl bromoacetate in the presence of a basic catalyst in an appropriate solvent.

As the basic catalyst, a super-strong basic catalyst such as sodium amide, sodium hydride, n-butyl lithium, and 1,8-diazabicyclo[5.4.0]undec-7-ene; strong basic catalyst such as methoxy potassium, ethoxy potassium, and t-butoxy potassium; weak basic catalyst such as triethylamine and tri-n-butyl amine; and the like can be given.

Of these basic catalysts, super-strong basic catalysts and strong basic catalysts are preferable. These basic catalysts may be used either individually or in combination of two or more.

As examples of the solvents, dimethylformamide, dimethylacetamide, dimethylsulfoxide, t-butanol, acetone, acetonitrile, tetrahydrofuran, chloroform, and methylene chloride can be given.

These solvents may be used either individually or in combination of two or more.

The reaction for synthesizing the carbazole derivative (1) is carried out at a temperature of usually −20° C. to 150° C., and preferably 0 to 70° C., for usually 1 minute to 96 hours, and preferably 30 minutes to 48 hours.

The carbazole derivative (1) is not only suitable particularly as an additive for increasing sensitivity of chemically amplified radiation-sensitive resin compositions used as a chemically amplified resist, but also can be used as an intermediate for synthesizing other carbazole derivatives having a carbazole ring structure.

Chemically Amplified Radiation-Sensitive Resin Composition

The other components for the chemically amplified radiation-sensitive resin composition of the present invention are not specifically limited in as much as the composition contains the carbazole derivative (1) as an essential component and can function as a chemically-amplified resist. The following chemically amplified radiation-sensitive resin composition can be given as a preferable example of such a composition.

A chemically amplified radiation sensitive resin composition comprising (A) the carbazole derivative (1), (B) an acid-dissociable group-containing resin which is insoluble or scarcely soluble in alkali, but becomes alkali soluble when the acid-dissociable group dissociates (hereinafter referred to as "acid-dissociable group-containing resin (B) "), and (C) a photoacid generator (hereinafter referred to as "acid generator (C) ") can be given as a preferable example (this resin composition is hereinafter referred to as "chemically amplified radiation sensitive resin composition [I]").

The chemically amplified radiation sensitive resin composition [I] will now be described.

Carbazole Derivative (1)

As the carbazole derivative (1) used as component (A) in the radiation-sensitive resin composition [I], compounds shown by the formulas (1-1), (1-6), (1-7), (1-8), (1-10), (1-20), (1-34), and (1-73) are particularly preferable.

The carbazole derivatives (I) can be used either individually or in combination of two or more in the chemically amplified radiation sensitive resin composition [I].

The amount of the carbazole derivatives (1) used in the chemically amplified radiation sensitive resin composition [I] is preferably 0.1–40 parts by weight, more preferably 0.2–20 parts by weight, and particularly preferably 1–10 parts by weight for 100 parts by weight of the acid-dissociable group-containing resin (B).

Acid-dissociable Group-containing Resin (B)

As the acid-dissociable group-containing resin (B), a resin, insoluble or scarcely soluble in alkali by itself, obtainable from an alkali-soluble resin containing one or more acid functional groups such as a phenolic hydroxyl group or carboxyl group by replacing one or more hydrogen atoms in the acid functional groups with acid-dissociable groups can be given.

If 50% or more of the initial film thickness of a resist film remains after development when a resist film made only from the acid-dissociable group-containing resin (B) is developed under the same alkaline development conditions employed for forming a resist pattern using a resist film formed from a radiation-sensitive resin composition comprising the acid-dissociable group-containing resin (B), such a characteristic of the acid-dissociable group-containing resin (B) is referred to as "insoluble or scarcely soluble in alkali" in the present invention.

As examples of such an acid-dissociable group in the acid-dissociable group-containing resin (B), a substituted methyl group, 1-substituted ethyl group, 1-branched alkyl group, silyl group, germyl group, alkoxycarbonyl group, acyl group, cyclic acid-dissociable group, and the like can be given.

As examples of the substituted methyl group, a methoxymethyl group, methylthiomethyl group, ethoxymethyl group, ethylthiomethyl group, methoxyethoxymethyl group, benzyloxymethyl group, benzylthiomethyl group, phenacyl group, bromophenacyl group, methoxyphenacyl group, methylthiophenacyl group, α-methylphenacyl group, cyclopropylmethyl group, benzyl group, diphenylmethyl group, triphenylmethyl group, bromobenzyl group, nitrobenzyl group, methoxybenzyl group, methylthiobenzyl group, ethoxybenzyl group, ethylthiobenzyl group, piperonyl group, methoxycarbonylmethyl group, ethoxycarbonylmethyl group, n-propoxycarbonylmethyl group, i-propoxycarbonylmethyl group, n-butoxycarbonylmethyl group, and t-butoxycarbonylmethyl group can be given.

As examples of the 1-substituted methyl group, a 1-methoxyethyl group, 1-methylthioethyl group, 1,1-dimethoxyethyl group, 1-ethoxyethyl group, 1-ethylthioethyl group, 1,1-diethoxyethyl group, 1-ethoxypropyl group, 1-propoxyethyl group, 1-cyclohexyloxyethyl group, 1-phenoxyethyl group, 1-phenylthioethyl group, 1,1-diphenoxyethyl group, 1-benzyloxyethyl group, 1-benzylthioethyl group, 1-cyclopropylethyl group, 1-phenylethyl group, 1,1-diphenylethyl group, 1-methoxycarbonylethyl group, 1-ethoxycarbonylethyl group, 1-n-propoxycarbonylethyl group, 1-i-propoxycarbonylethyl group, 1-n-butoxycarbonylethyl group, and 1-t-butoxycarbonylethyl group can be given.

As examples of the 1-branched alkyl group, an i-propyl group, sec-butyl group, t-butyl group, 1,1-dimethylpropyl group, 1-methylbutyl group, and 1,1-dimethylbutyl group can be given.

As examples of the silyl groups, tricarbylsilyl groups such as a trimethylsilyl group, ethyldimethylsilyl group, methyldiethylsilyl group, triethylsilyl group, i-propyldimethylsilyl group, methyldi-1-propylsilyl group, tri-i-propylsilyl group, t-butyldimethylsilyl group, methyldi-t-butylsilyl group, tri-t-butylsilyl group, phenyldimethylsilyl group, methyldiphenylsilyl group, and triphenylsilyl group can be given.

As examples of the germyl group, tricarbylgermyl groups such as a trimethylgermyl group, ethyldimethylgermyl group, methyldiethylgermyl group, triethylgermyl group, i-propyldimethylgermyl group, methyldi-i-propylgermyl group, tri-i-propylgermyl group, t-butyldimethylgermyl group, methyldi-t-butylgermyl group, tri-t-butylgermyl group, phenyldimethylgermyl group, methyldiphenylgermyl group, and triphenylgermyl group can be given.

As examples of the alkoxycarbonyl group, a methoxycarbonyl group, ethoxycarbonyl group, i-propoxycarbonyl group, and t-butoxycarbonyl group can be given.

As examples of the acyl group, an acetyl group, propionyl group, butyryl group, heptanoyl group, hexanoyl group, valeryl group, pivaloyl group, isovaleryl group, lauroyl group, myristoyl group, palmitoyl group, stearoyl group, oxalyl group, malonyl group, succinyl group, glutaryl group, adipoyl group, piperoyl group, suberoyl group, azelaoyl group, sebacoyl group, acryloyl group, propioloyl group, methacryloyl group, crotonoyl group, oleoyl group, maleoyl group, fumaroyl group, mesaconoyl group, campholoyl group, benzoyl group, phthaloyl group, isophthaloyl group, terephthaloyl group, naphthoyl group, toluoyl group, hydroatropoyl group, atropoyl group, cinnamoyl group, furoyl group, thenoyl group, nicotinoyl group, isonicotinoyl group, p-toluenesulfonyl group, and mesyl group can be given.

As examples of the cyclic acid-dissociable group, a cyclopropyl group, cyclopentyl group, cyclohexyl group, cyclohexenyl group, 4-methoxycyclohexyl group, tetrahydropyranyl group, tetrahydrofuranyl group, tetrahydrothiofuranyl group, tetrahydrothiopyranyl group, 3-bromotetrahydropyranyl group, 4-methoxytetrahydropyranyl group, 4-methoxytetrahydrothiopyranyl group, and 3-tetrahydrothiophene-1,1-dioxide group can be given.

Of these acid-dissociable groups, a t-butyl group, benzyl group, 1-methoxyethyl group, 1-ethoxyethyl group, trimethylsilyl group, t-butoxycarbonyl group, t-butoxycarbonylmethyl group, tetrahydrofuranyl group, tetrahydropyranyl group, tetrahydrothiofuranyl group, tetrahydrothiopyranyl group, and the like are preferable.

As particularly preferable acid-dissociable group-containing resin (B) of the present invention, a resin obtainable from a poly(p-hydroxystyrene), a copolymer of p-hydroxystyrene and p-hydroxy-α-methylstyrene, a copolymer of p-hydroxy styrene and styrene, or a copolymer of p-hydroxy styrene and/or p-hydroxy-α-methylstyrene, and (meth) acrylic acid by replacing a part or all of the hydrogen atoms in the phenolic hydroxyl groups or the hydrogen atoms in the carboxylic groups with the above-mentioned acid-dissociable groups, particularly with a group selected from the group consisting of a t-butyl group, benzyl group, 1-methoxyethyl group, 1-ethoxyethyl group, trimethylsilyl group, t-butoxycarbonyl group, t-butoxycarbonylmethyl group, tetrahydropyranyl group, tetrahydrofuranyl group, tetrahydrothiopyranyl group, and tetrahydrothiofuranyl group can be given.

The amount of the acid-dissociable groups introduced into the acid-dissociable group-containing resin (B) (the amount of the number of the acid-dissociable groups in the total number of non-protected acid functional groups and acid-dissociable groups in the acid-dissociable group-containing resin (B)) is preferably 10–100%, and still more preferably 15–100%, although the amount varies depending on the types of acid-dissociable groups and the alkali-soluble resin into which the acid-dissociable groups are introduced.

The polystyrene-reduced weight average molecular weight (hereinafter referred to as "Mw") of the acid-dissociable group-containing resin (B) determined by gel permeation chromatography (GPC) is preferably 1,000–150,000, and more preferably 3,000–100,000.

The ratio of Mw to the polystyrene-reduced number average molecular weight (hereinafter referred to as "Mn") determined by gel permeation chromatography (Mw/Mn) of the acid-dissociable group-containing resin (B) is usually 1–10, and preferably 1–5.

The acid-dissociable group-containing resin (B) can be prepared, for example, by introducing one or more acid-dissociable groups into an alkali-soluble resin, by (co) polymerization of monomers containing one or more acid-dissociable groups, or by (co)polycondensation of polycondensable components containing one or more acid-dissociable groups.

The acid-dissociable group-containing resin (B) can be used either individually or in combination of two or more, or in combination with one or more alkali-soluble resins such as a poly(p-hydroxystyrene) or a novolak resin in the chemically amplified radiation sensitive resin composition [I].

Acid Generator (C)

The photoacid generator (C) of the present invention is a component which generates an acid upon exposure.

As such an acid generator (C), (1) onium salt compounds, (2) sulfone compounds, (3) sulfonate compounds, (4) sulfonimide compounds, (5) disulfonyldiazomethane compounds, (6) disulfonylmethane compounds, (7) oxime-sulfonate compounds, (8) hydrazine sulfonate compounds, and the like can be given.

Examples of these acid generators (C) are as follows;

(1) Onium Salt Compounds:

As examples of onium salt compounds, iodonium salts, sulfonium salts (including thiophenium salts), phosphonium salts, diazonium salts, ammonium salts, and pyridinium salts can be given.

Specific examples of onium salts include: bis(4-t-butylphenyl)iodonium trifluoromethanesulfonate,
bis(4-t-butylphenyl)iodonium nonafluoro-n-butanesulfonate,
bis(4-t-butylphenyl)iodonium perfluoro-n-octanesulfonate,
bis(4-t-butylphenyl)iodonium pyrenesulfonate,
bis (4-t-butylphenyl)iodonium n-dodecylbenzenesulfonate,
bis(4-t-butylphenyl)iodonium p-toluenesulfonate,
bis(4-t-butylphenyl)iodonium benzenesulfonate,
bis(4-t-butylphenyl)iodonium 10-camphorsulfonate,
bis(4-t-butylphenyl)iodonium n-octanesulfonate,
bis(4-t-butylphenyl)iodonium 2-trifluoromethylbenzenesulfonate,
bis(4-t-butylphenyl)iodonium 4-trifluoromethylbenzenesulfonate,
bis(4-t-butylphenyl)iodonium perfluorobenzenesulfonate,
diphenyliodonium trifluoromethanesulfonate,
diphenyliodonium nonafluoro-n-butanesulfonate,
diphenyliodonium perfluoro-n-octanesulfonate,
diphenyliodonium pyrenesulfonate,
diphenyliodonium n-dodecylbenzenesulfonate,
diphenyliodonium p-toluenesulfonate, diphenyliodonium benzenesulfonate,
diphenyliodonium 10-camphorsulfonate,
diphenyliodonium n-octanesulfonate,
diphenyliodonium 2-trifluoromethylbenzenesulfonate,
diphenyliodonium 4-trifluoromethylbenzenesulfonate,
diphenyliodonium perfluorobenzenesulfonate,
di(p-tolyl)iodonium trifluoromethanesulfonate,
di(p-tolyl)iodonium nonafluoro-n-butanesulfonate,
di(p-tolyl)iodonium perfluoro-n-octanesulfonate,
di (p-tolyl)iodonium pyrenesulfonate,
di(p-tolyl)iodonium n-dodecylbenzenesulfonate,
di(p-tolyl)iodonium p-toluenesulfonate, di(p-tolyl)iodonium benzenesulfonate,
di(p-tolyl)iodonium 10-camphorsulfonate,
di(p-tolyl)iodonium n-octanesulfonate,
di(p-tolyl)iodonium 2-trifluoromethylbenzenesulfonate,
di(p-tolyl)iodonium 4-trifluoromethylbenzenesulfonate,
di(p-tolyl)iodonium perfluorobenzenesulfonate,
di(3,4-dimethylphenyl)iodonium trifluoromethanesulfonate,
di(3,4-dimethylphenyl)iodonium nonafluoro-n-butanesulfonate,
di(3,4-dimethylphenyl)iodonium perfluoro-n-octanesulfonate,
di(3,4-dimethylphenyl)iodonium pyrenesulfonate,
di(3,4-dimethylphenyl)iodonium n-dodecylbenzenesulfonate,
di(3,4-dimethylphenyl)iodonium p-toluenesulfonate,
di(3,4-dimethylphenyl)iodonium benzenesulfonate,
di(3,4-dimethylphenyl)iodonium 10-camphorsulfonate,
di(3,4-dimethylphenyl)iodonium n-octanesulfonate,
di(3,4-dimethylphenyl)iodonium 2-trifluoromethylbenzenesulfonate,
di(3,4-dimethylphenyl)iodonium 4-trifluoromethylbenzenesulfonate,
di(3,4-dimethylphenyl)iodonium perfluorobenzenesulfonate,
p-nitrophenyl·phenyliodonium trifluoromethanesulfonate,
p-nitrophenyl·phenyliodonium nonafluoro-n-butanesulfonate,
p-nitrophenyl·phenyliodonium perfluoro-n-octanesulfonate,
p-nitrophenyl·phenyliodonium pyrenesulfonate,
p-nitrophenyl·phenyliodonium-dodecylbenzenesulfonate,
p-nitrophenyl·phenyliodonium p-toluenesulfonate,
p-nitrophenyl·phenyliodonium benzenesulfonate,
p-nitrophenyl·phenyliodonium 10-camphorsulfonate,
p-nitrophenyl·phenyliodonium n-octanesulfonate,
p-nitrophenyl·phenyliodonium 2-trifluoromethylbenzenesulfonate,
p-nitrophenyl·phenyliodonium 4-trifluoromethylbenzenesulfonate,
p-nitrophenyl·phenyliodonium perfluorobenzenesulfonate,
di(m-nitrophenyl)iodonium trifluoromethanesulfonate,
di(m-nitrophenyl)iodonium nonafluoro-n-butanesulfonate,
di(m-nitrophenyl)iodonium perfluoro-n-octanesulfonate,
di(m-nitrophenyl)iodonium pyrenesulfonate,
di(m-nitrophenyl)iodonium n-dodecylbenzenesulfonate,
di(m-nitrophenyl)iodonium p-toluenesulfonate,
di(m-nitrophenyl)iodonium benzenesulfonate,
di(m-nitrophenyl)iodonium 10-camphorsulfonate,
di(m-nitrophenyl)iodonium n-octanesulfonate,
di(m-nitrophenyl)iodonium 2-trifluoromethylbenzenesulfonate,
di(m-nitrophenyl)iodonium 4-trifluoromethylbenzenesulfonate,
di(m-nitrophenyl)iodonium perfluorobenzenesulfonate,
p-methoxyphenyl·phenyl iodonium trifluoromethanesulfonate,
p-methoxyphenyl·phenyliodonium nonafluoro-n-butanesulfonate,
p-methoxyphenyl·phenyliodonium perfluoro-n-octanesulfonate,
p-methoxyphenyl·phenyliodonium pyrenesulfonate,
p-methoxyphenyl·phenyliodonium n-dodecylbenzenesulfonate,
p-methoxyphenyl·phenyliodonium p-toluenesulfonate,
p-methoxyphenyl·phenyliodonium benzenesulfonate,
p-methoxyphenyl·phenyliodonium 10-camphorsulfonate,
p-methoxyphenyl·phenyliodonium n-octanesulfonate,
p-methoxyphenyl·phenyliodonium 2-trifluoromethylbenzenesulfonate,
p-methoxyphenyl·phenyliodonium 4-trifluoromethylbenzenesulfonate,
p-methoxyphenyl·phenyliodonium perfluorobenzenesulfonate,
di(p-chlorophenyl) iodoniumtrifluoromethane sulfonate,
di(p-chlorophenyl)iodonium nonafluoro-n-butanesulfonate,
di(p-chlorophenyl)iodonium perfluoro-n-octanesulfonate,
di(p-chlorophenyl)iodonium pyrenesulfonate,
di(p-chlorophenyl)iodonium n-dodecylbenzenesulfonate,
di(p-chlorophenyl)iodonium p-toluenesulfonate,
di(p-chlorophenyl)iodonium benzenesulfonate,
di(p-chlorophenyl)iodonium 10-camphorsulfonate,
di(p-chlorophenyl)iodonium n-octanesulfonate,
di(p-chlorophenyl)iodonium 2-trifluoromethylbenzenesulfonate,
di(p-chlorophenyl)iodonium 4-trifluoromethylbenzenesulfonate,
di(p-chlorophenyl)iodonium perfluorobenzenesulfonate,
di(p-trifluoromethylphenyl)iodonium trifluoromethanesulfonate,
di(p-trifluoromethylphenyl)iodonium nonafluoro-n-butanesulfonate,
di(p-trifluoromethylphenyl)iodonium perfluoro-n-octanesulfonate,
di(p-trifluoromethylphenyl)iodonium pyrenesulfonate,
di(p-trifluoromethylphenyl)iodonium n-dodecylbenzenesulfonate,
di(p-trifluoromethylphenyl)iodonium p-toluenesulfonate,
di(p-trifluoromethylphenyl)iodonium benzenesulfonate,
di(p-trifluoromethylphenyl)iodonium 10-camphorsulfonate,
di(p-trifluoromethylphenyl)iodonium n-octanesulfonate,
di(p-trifluoromethylphenyl)iodonium 2-trifluoromethylbenzenesulfonate,
di(p-trifluoromethylphenyl)iodonium 4-trifluoromethylbenzenesulfonate,
di(p-trifluoromethylphenyl)iodonium perfluorobenzenesulfonate,
dinaphthyliodonium trifluoromethanesulfonate,
dinaphthyliodonium nonafluoro-n-butanesulfonate,
dinaphthyliodonium perfluoro-n-octanesulfonate,
dinaphthyliodonium pyrenesulfonate,
dinaphthyliodonium n-dodecylbenzenesulfonate,
dinaphthyliodonium p-toluenesulfonate,
dinaphthyliodonium benzenesulfonate,
dinaphthyliodonium 10-camphorsulfonate,
dinaphthyliodonium n-octanesulfonate,
dinaphthyliodonium 2-trifluoromethylbenzenesulfonate,
dinaphthyliodonium 4-trifluoromethylbenzenesulfonate,
dinaphthyliodonium perfluorobenzenesulfonate,
biphenyleneiodonium trifluoromethanesulfonate,
biphenyleneiodonium nonafluoro-n-butanesulfonate,
biphenyleneiodonium perfluoro-n-octanesulfonate,
biphenyleneiodonium pyrenesulfonate,
biphenyleneiodonium n-dodecylbenzenesulfonate,
biphenyleneiodonium p-toluenesulfonate,
biphenyleneiodonium benzenesulfonate,
biphenyleneiodonium 10-camphorsulfonate,
biphenyleneiodonium n-octanesulfonate,
biphenyleneiodonium 2-trifluoromethylbenzenesulfonate,
biphenyleneiodonium 4-trifluoromethylbenzenesulfonate,
biphenyleneiodonium perfluorobenzenesulfonate,
2-chlorobiphenyleneiodonium trifluoromethanesulfonate,
2-chlorobiphenyleneiodonium nonafluoro-n-butanesulfonate,
2-chlorobiphenyleneiodonium perfluoro-n-octanesulfonate,
2-chlorobiphenyleneiodonium pyrenesulfonate,
2-chlorobiphenyleneiodonium n-dodecylbenzenesulfonate, 2-chlorobiphenyleneiodonium p-toluenesulfonate,
2-chlorobiphenyleneiodonium benzenesulfonate,
2-chlorobiphenyleneiodonium 10-camphorsulfonate,
2-chlorobiphenyleneiodonium n-octanesulfonate,
2-chlorobiphenyleneiodonium 2-trifluoromethylbenzenesulfonate,
2-chlorobiphenyleneiodonium 4-trifluoromethylbenzenesulfonate,
2-chlorobiphenyleneiodonium perfluorobenzenesulfonate,
triphenylsulfonium trifluoromethanesulfonate,
triphenylsulfonium nonafluoro-n-butanesulfonate,
triphenylsulfonium perfluoro-n-octanesulfonate,
triphenylsulfonium pyrenesulfonate,
triphenylsulfonium n-dodecylbenzenesulfonate,
triphenylsulfonium p-toluenesulfonate,
triphenylsulfonium benzenesulfonate,
triphenylsulfonium 10-camphorsulfonate,
triphenylsulfonium n-octanesulfonate,
triphenylsulfonium 2-trifluoromethylbenzenesulfonate,
triphenylsulfonium 4-trifluoromethylbenzenesulfonate,
triphenylsulfonium hexafluoroantimonate,
triphenylsulfonium naphthalenesulfonate,
triphenylsulfonium perfluorobenzenesulfonate,
4-t-butylphenyl·diphenylsulfonium trifluoromethanesulfonate,
4-t-butylphenyl·diphenylsulfonium nonafluoro-n-butanesulfonate,
4-t-butylphenyl·diphenylsulfonium perfluoro-n-octanesulfonate,
4-t-butylphenyl·diphenylsulfonium pyrenesulfonate,
4-t-butylphenyl·diphenylsulfonium n-dodecylbenzenesulfonate,
4-t-butylphenyl·diphenylsulfonium p-toluenesulfonate,
4-t-butylphenyl·diphenylsulfonium benzenesulfonate,
4-t-butylphenyl·diphenylsulfonium 10-camphorsulfonate,
4-t-butylphenyl·diphenylsulfonium n-octanesulfonate,
4-t-butylphenyl·diphenylsulfonium 2-trifluoromethylbenzenesulfonate,
4-t-butylphenyl·diphenylsulfonium 4-trifluoromethanebenzenesulfonate,
4-t-butylphenyl·diphenylsulfonium perfluorobenzenesulfonate,
4-t-butoxyphenyl·diphenylsulfonium trifluoromethanesulfonate,
4-t-butoxyphenyl·diphenylsulfonium nonafluoro-n-butanesulfonate,
4-t-butoxyphenyl·diphenylsulfonium perfluoro-n-octanesulfonate,
4-t-butoxyphenyl·diphenylsulfonium pyrenesulfonate,
4-t-butoxyphenyl·diphenylsulfonium n-dodecylbenzenesulfonate,
4-t-butoxyphenyl·diphenylsulfonium p-toluenesulfonate,
4-t-butoxyphenyl·diphenylsulfonium benzenesulfonate,
4-t-butoxyphenyl·diphenylsulfonium 10-camphorsulfonate,
4-t-butoxyphenyl·diphenylsulfonium n-octanesulfonate,
4-t-butoxyphenyl·diphenylsulfonium 2-trifluoromethylbenzenesulfonate,
4-t-butoxyphenyl·diphenylsulfonium 4-trifluoromethylbenzenesulfonate,
4-t-butoxyphenyl·diphenylsulfonium perfluorobenzenesulfonate,
4-hydroxyphenyl·diphenylsulfonium trifluoromethanesulfonate,
4-hydroxyphenyl·diphenylsulfonium nonafluoro-n-butanesulfonate,
4-hydroxyphenyl·diphenylsulfonium perfluoro-n-octanesulfonate,
4-hydroxyphenyl·diphenylsulfonium pyrenesulfonate,
4-hydroxyphenyl·diphenylsulfonium n-dodecylbenzenesulfonate,
4-hydroxyphenyl·diphenylsulfonium p-toluenesulfonate,
4-hydroxyphenyl·diphenylsulfonium benzenesulfonate,
4-hydroxyphenyl·diphenylsulfonium 10-camphorsulfonate,
4-hydroxyphenyl·diphenylsulfonium n-octanesulfonate,
4-hydroxyphenyl·diphenylsulfonium 2-trifluoromethylbenzenesulfonate,
4-hydroxyphenyl·diphenylsulfonium 4-trifluoromethylbenzenesulfonate,
4-hydroxyphenyl·diphenylsulfonium perfluorobenzenesulfonate,
tri(p-methoxyphenyl)sulfonium trifluoromethanesulfonate,
tri(p-methoxyphenyl)sulfonium nonafluoro-n-butanesulfonate,
tri(p-methoxyphenyl)sulfonium perfluoro-n-octanesulfonate,
tri(p-methoxyphenyl)sulfonium pyrenesulfonate,
tri(p-methoxyphenyl)sulfonium n-dodecylbenzenesulfonate,
tri(p-methoxyphenyl)sulfonium p-toluenesulfonate,
tri(p-methoxyphenyl)sulfonium benzenesulfonate,
tri(p-methoxyphenyl)sulfonium 10-camphorsulfonate,
tri(p-methoxyphenyl)sulfonium n-octanesulfonate,
tri(p-methoxyphenyl)sulfonium 2-trifluoromethylbenzenesulfonate,
tri(p-methoxyphenyl)sulfonium 4-trifluoromethylbenzenesulfonate,
tri(p-methoxyphenyl)sulfonium perfluorobenzenesulfonate,
di(p-methoxyphenyl)·p-tolylsulfonium trifluoromethanesulfonate,
di(p-methoxyphenyl)·p-tolylsulfonium nonafluoro-n-butanesulfonate,
di(p-methoxyphenyl)·p-tolylsulfonium perfluoro-n-octanesulfonate,
di(p-methoxyphenyl)·p-tolylsulfonium pyrenesulfonate,
di(p-methoxyphenyl)·p-tolylsulfonium n-dodecylbenzenesulfonate,
di(p-methoxyphenyl)·p-tolylsulfonium p-toluenesulfonate,
di(p-methoxyphenyl)·p-tolylsulfonium benzenesulfonate,
di(p-methoxyphenyl)·p-tolylsulfonium 10-camphorsulfonate,
di(p-methoxyphenyl)·p-tolylsulfonium n-octanesulfonate,
di(p-methoxyphenyl)·p-tolylsulfonium 2-trifluoromethylbenzenesulfonate,
di(p-methoxyphenyl)·p-tolylsulfonium 4-trifluoromethylbenzenesulfonate,
di(p-methoxyphenyl)·p-tolylsulfonium perfluorobenzenesulfonate,
phenyl·tetramethylenesulfonium trifluoromethanesulfonate,
phenyl·tetramethylenesulfonium nonafluoro-n-butanesulfonate,
phenyl·tetramethylenesulfonium perfluoro-n-octanesulfonate,
phenyl·tetramethylenesulfonium pyrenesulfonate,
phenyl·tetramethylenesulfonium n-dodecylbenzenesulfonate,
phenyl·tetramethylenesulfonium p-toluenesulfonate,
phenyl·tetramethylenesulfonium benzenesulfonate,
phenyl·tetramethylenesulfonium 10-camphorsulfonate,
phenyl·tetramethylenesulfonium n-octanesulfonate,
phenyl·tetramethylenesulfonium 2-trifluoromethylbenzenesulfonate,
phenyl·tetramethylenesulfonium 4-trifluoromethylbenzenesulfonate,
phenyl·tetramethylenesulfonium perfluorobenzenesulfonate, p-hydroxyphenyl·tetramethylenesulfonium trifluoromethanesulfonate,
p-hydroxyphenyl·tetramethylenesulfonium nonafluoro-n-butanesulfonate,
p-hydroxyphenyl·tetramethylenesulfonium perfluoro-n-octanesulfonate,
p-hydroxyphenyl·tetramethylenesulfonium pyrenesulfonate,
p-hydroxyphenyl·tetramethylenesulfonium n-dodecylbenzenesulfonate,
p-hydroxyphenyl·tetramethylenesulfonium p-toluenesulfonate,
p-hydroxyphenyl·tetramethylenesulfonium benzenesulfonate,
p-hydroxyphenyl·tetramethylenesulfonium 10-camphorsulfonate,
p-hydroxyphenyl·tetramethylenesulfonium n-octanesulfonate,
p-hydroxyphenyl·tetramethylenesulfonium 2-trifluoromethylbenzenesulfonate,
p-hydroxyphenyl·tetramethylenesulfonium 4-trifluoromethylbenzenesulfonate,
p-hydroxyphenyl·tetramethylenesulfonium perfluorobenzenesulfonate,
phenyl·biphenylenesulfonium trifluoromethanesulfonate,
phenyl·biphenylenesulfonium nonafluoro-n-butanesulfonate,
phenyl·biphenylenesulfonium perfluoro-n-octanesulfonate,
phenyl·biphenylenesulfonium pyrenesulfonate,
phenyl·biphenylenesulfonium n-dodecylbenzenesulfonate,
phenyl·biphenylenesulfonium p-toluenesulfonate,
phenyl·biphenylenesulfonium benzenesulfonate,
phenyl·biphenylenesulfonium 10-camphorsulfonate,
phenyl·biphenylenesulfonium n-octanesulfonate,
phenyl·biphenylenesulfonium 2-trifluoromethylbenzenesulfonate,
phenyl·biphenylenesulfonium 4-trifluoromethylbenzenesulfonate,
phenyl·biphenylenesulfonium perfluorobenzenesulfonate,
(4-phenylthiophenyl)·diphenylsulfonium trifluoromethanesulfonate,
(4-phenylthiophenyl)·diphenylsulfonium nonafluoro-n-butanesulfonate,
(4-phenylthiophenyl)·diphenylsulfonium perfluoro-n-octanesulfonate,
(4-phenylthiophenyl)·diphenylsulfonium pyrenesulfonate,
(4-phenylthiophenyl)·diphenylsulfonium n-dodecylbenzenesulfonate,
(4-phenylthiophenyl)·diphenylsulfonium p-toluenesulfonate,
(4-phenylthiophenyl)·diphenylsulfonium benzenesulfonate,
(4-phenylthiophenyl)·diphenylsulfonium 10-camphorsulfonate,
(4-phenylthiophenyl)·diphenylsulfonium n-octanesulfonate,
(4-phenylthiophenyl)·diphenylsulfonium 2-trifluoromethylbenzenesulfonate,
(4-phenylthiophenyl)·diphenylsulfonium 4-trifluoromethylbenzenesulfonate,
(4-phenylthiophenyl)·diphenylsulfonium perfluorobenzenesulfonate,
4,4'-bis(diphenylsulfoniophenyl)sulfide di(trifluoromethanesulfonate),
4,4'-bis(diphenylsulfoniophenyl)sulfide di(nonafluoro-n-butanesulfonate),
4,4'-bis(diphenylsulfoniophenyl)sulfide di(perfluoro-n-octanesulfonate),
4,4'-bis(diphenylsulfoniophenyl)sulfide di(pyrenesulfonate),
4,4'-bis(diphenylsulfoniophenyl)sulfide di(n-dodecylbenzenesulfonate),
4,4'-bis(diphenylsulfoniophenyl)sulfide di(p-toluenesulfonate),
4,4'-bis(diphenylsulfoniophenyl)sulfide di(benzenesulfonate),
4,4'-bis(diphenylsulfoniophenyl)sulfide di(10-camphorsulfonate),
4,4'-bis(diphenylsulfoniophenyl)sulfide di(n-octanesulfonate),
4,4'-bis(diphenylsulfoniophenyl)sulfide di(2-trifluoromethylbenzenesulfonate),
4,4'-bis(diphenylsulfoniophenyl)sulfide di(4-trifluoromethylbenzenesulfonate),
4,4'-bis(diphenylsulfoniophenyl)sulfide di(perfluorobenzenesulfonate), and the like.

(2) Sulfone Compounds:

As examples of sulfone compounds, β-ketosulfone, β-sulfonylsulfone, and α-diazo compounds of these compounds can be given.

As specific examples of sulfone compounds, phenacylphenylsulfone, mesitylphenacylsulfone, bis(phenylsulfonyl)methane, and 4-trisphenacylsulfone can be given.

(3) Sulfonate Compounds:

As examples of sulfonate compounds, alkyl sulfonate, haloalkyl sulfonate, aryl sulfonate, and imino sulfonate can be given.

As specific examples of sulfonate compounds, benzointosylate, pyrogallol tris (trifluoromethanesulfonate), pyrogallol tris(nonafluorobutanesulfonate), pyrogallol tris (methanesulfonate), nitrobenzyl-9,10-diethoxyanthracene-2-sulfonate, α-methylolbenzointosylate, α-methylolbenzoin trifluoromethanesulfonate, α-methylolbenzoin n-octanesulfonate, and α-methylolbenzoin n-dodecanesulfonate can be given.

(4) Sulfonimide Compounds:

As examples of sulfonimide compounds, compounds of the following formula (2) can be given:

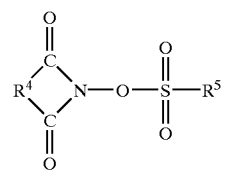

(2)

wherein $R^4$ represents a divalent group such as an alkylene group, arylene group, and alkoxylene group, and $R^5$ represents a monovalent group such as an alkyl group, aryl group, halogenated alkyl group, and halogenated aryl group.

Specific examples of sulfonimide compounds include:
N-(trifluoromethanesulfonyloxy)succinimide,
N-(trifluoromethanesulfonyloxy)phthalimide,
N-(trifluoromethanesulfonyloxy)diphenylmaleimide,
N-(trifluoromethanesulfonyloxy)bicyclo[2.2.1]hept-5-ene-2,3-dicarboxyimide,
N-(trifluoromethanesulfonyloxy)-7-oxabicyclo[2.2.1]hept-5-ene-2,3-dicarboxyimide,
N-(trifluoromethanesulfonyloxy)bicyclo[2.2.1]heptan-5,6-oxy-2,3-dicarboxyimide,
N-(trifluoromethanesulfonyloxy)naphthylimide,
N-(10-camphorsulfonyloxy)succinimide,
N-(10-camphorsulfonyloxy)phthalimide,
N-(10-camphorsulfonyloxy)diphenylmaleimide,
N-(10-camphorsulfonyloxy)bicyclo[2.2.1]hept-5-ene-2,3-dicarboxyimide, N-(10-camphorsulfonyloxy)-7-oxabicyclo[2.2.1]hept-5-ene-2,3-dicarboxyimide,
N-(10-camphorsulfonyloxy)bicyclo[2.2.1]heptan-5,6-oxy-2,3-dicarboxyimide,
N-(10-camphorsulfonyloxy)naphthylimide,
N-(n-octanesulfonyloxy)succinimide,
N-(n-octanesulfonyloxy)phthalimide,
N-(n-octanesulfonyloxy)diphenylmaleimide,
N-(n-octanesulfonyloxy)bicyclo[2.2.1]hept-5-ene-2,3-dicarboxyimide,
N-(n-octanesulfonyloxy)-7-oxabicyclo[2.2.1]hept-5-ene-2,3-dicarboxyimide,
N-(n-octanesulfonyloxy)bicyclo[2.2.1]heptan-5,6-oxy-2,3-dicarboxyimide,
N-(n-octanesulfonyloxy)naphthylimide,
N-(p-toluenesulfonyloxy)succinimide,
N-(p-toluenesulfonyloxy)phthalimide,
N-(p-toluenesulfonyloxy)diphenylmaleimide,
N-(p-toluenesulfonyloxy)bicyclo[2.2.1]hept-5-ene-2,3-dicarboxyimide,
N-(p-toluenesulfonyloxy)-7-oxabicyclo[2.2.1]hept-5-ene-2,3-dicarboxyimide,
N-(p-toluenesulfonyloxy)bicyclo[2.2.1]heptan-5,6-oxy-2,3-dicarboxyimide,
N-(p-toluenesulfonyloxy)naphthylimide,
N-(2-trifluoromethylbenzenesulfonyloxy)succinimide,
N-(2-trifluoromethylbenzenesulfonyloxy)phthalimide,
N-(2-trifluoromethylbenzenesulfonyloxy)diphenylmaleimide,
N-(2-trifluoromethylbenzenesulfonyloxy)bicyclo[2.2.1]hept-5-ene-2,3-dicarboxyimide,
N-(2-trifluoromethylbenzenesulfonyloxy)-7-oxabicyclo[2.2.1]hept-5-ene-2,3-dicarboxyimide,
N-(2-trifluoromethylbenzenesulfonyloxy)bicyclo[2.2.1]heptane-5,6-oxy-2,3-dicarboxyimide,
N-(2-trifluoromethylbenzenesulfonyloxy)naphthylimide,
N-(4-trifluoromethylbenzenesulfonyloxy)succinimide,
N-(4-trifluoromethylbenzenesulfonyloxy)phthalimide,
N-(4-trifluoromethylbenzenesulfonyloxy)diphenylmaleimide,
N-(4-trifluoromethylbenzenesulfonyloxy)bicyclo[2.2.1]hept-5-ene-2,3-dicarboxyimide,
N-(4-trifluoromethylbenzenesulfonyloxy)-7-oxabicyclo[2.2.1]hept-5-ene-2,3-dicarboxyimide,
N-(4-trifluoromethylbenzenesulfonyloxy)bicyclo[2.2.1]heptane-5,6-oxy-2,3-dicarboxyimide,
N-(4-trifluoromethylbenzenesulfonyloxy)naphthylimide,
N-(perfluorobenzenesulfonyloxy)succinimide,
N-(perfluorobenzenesulfonyloxy)phthalimide,
N-(perfluorobenzenesulfonyloxy)diphenylmaleimide,
N-(perfluorobenzenesulfonyloxy)bicyclo[2.2.1]hept-5-ene-2,3-dicarboxyimide,
N-(perfluorobenzenesulfonyloxy)-7-oxabicyclo[2.2.1]hept-5-ene-2,3-dicarboxyimide,
N-(perfluorobenzenesulfonyloxy)bicyclo[2.2.1]heptan-5,6-oxy-2,3-dicarboxyimide,
N-(perfluorobenzenesulfonyloxy)naphthylimide,
N-(naphthalenesulfonyloxy)succinimide,
N-(naphthalenesulfonyloxy)phthalimide,
N-(naphthalenesulfonyloxy)diphenylmaleimide,
N-(naphthalenesulfonyloxy)bicyclo[2.2.1]hept-5-ene-2,3-dicarboxyimide,
N-(naphthalenesulfonyloxy)-7-oxabicyclo[2.2.1]hept-5-ene-2,3-dicarboxyimide,
N-(naphthalenesulfonyloxy)bicyclo[2.2.1]heptan-5,6-oxy-2,3-dicarboxyimide,
N-(naphthalenesulfonyloxy)naphthylimide,
N-(nonafluoro-n-butanesulfonyloxy)succinimide,
N-(nonafluoro-n-butanesulfonyloxy)phthalimide,
N-(nonafluoro-n-butanesulfonyloxy)diphenylmaleimide,
N-(nonafluoro-n-butanesulfonyloxy)bicyclo[2.2.1]hept-5-ene-2,3-dicarboxyimide,
N-(nonafluoro-n-butanesulfonyloxy)-7-oxabicyclo[2.2.1]hept-5-ene-2,3-dicarboxyimide,
N-(nonafluoro-n-butanesulfonyloxy)bicyclo[2.2.1]heptan-5,6-oxy-2,3-dicarboxyimide,
N-(nonafluoro-n-butanesulfonyloxy)naphthylimide,
N-(perfluoro-n-octanesulfonyloxy)succinimide,
N-(perfluoro-n-octanesulfonyloxy)phthalimide,
N-(perfluoro-n-octanesulfonyloxy)diphenylmaleimide,
N-(perfluoro-n-octanesulfonyloxy)bicyclo[2.2.1]hept-5-ene-2,3-dicarboxyimide,
N-(perfluoro-n-octanesulfonyloxy)-7-oxabicyclo[2.2.1]hept-5-ene-2,3-dicarboxyimide,
N-(perfluoro-n-octanesulfonyloxy)bicyclo[2.2.1]heptan-5,6-oxy-2,3-dicarboxyimide,
N-(perfluoro-n-octanesulfonyloxy)naphthylimide,
N-(benzenesulfonyloxy)succinimide,
N-(benzenesulfonyloxy)phthalimide,
N-(benzenesulfonyloxy)diphenylmaleimide,
N-(benzenesulfonyloxy)bicyclo[2.2.1]hept-5-ene-2,3-dicarboxyimide,
N-(benzenesulfonyloxy)-7-oxabicyclo[2.2.1]hept-5-ene-2,3-dicarboxyimide,
N-(benzenesulfonyloxy)bicyclo[2.2.1]heptan-5,6-oxy-2,3-dicarboxyimide,
N-(benzenesulfonyloxy)naphthylimide, and the like.

(5) Disulfonyldiazomethane Compounds:

As examples of disulfonyldiazomethane compounds, a compound shown by the following formula (3) can be given:

$$R^6-\underset{\underset{O}{\|}}{\overset{\overset{O}{\|}}{S}}-\underset{}{\overset{N_2}{\|}}{C}-\underset{\underset{O}{\|}}{\overset{\overset{O}{\|}}{S}}-R^7 \qquad (3)$$

wherein $R^6$ and $R^7$ individually represent a monovalent group such as an alkyl group, aryl group, halogenated alkyl group, and halogenated aryl group.

The following compounds can be given as specific examples of disulfonyldiazomethane compounds:
bis(trifluoromethanesulfonyl)diazomethane,
bis(cyclohexanesulfonyl)diazomethane,
bis(phenylsulfonyl)diazomethane,
bis(p-toluenesulfonyl)diazomethane,
bis(2,4-dimethylbenzenesulfonyl)diazomethane,
methylsulfonyl-p-toluenesulfonyldiazomethane,
bis(p-t-butylphenylsulfonyl)diazomethane,
bis(p-chlorobenzenesulfonyl)diazomethane,
cyclohexylsulfonyl·p-toluenesulfonyldiazomethane,
1-cyclohexylsulfonyl·1,1-dimethylethylsulfonyldiazomethane bis(1,1-dimethylethylsulfonyl)diazomethane,
bis(1-methylethylsulfonyl)diazomethane,
bis(3,3-dimethyl-1,5-dioxaspiro[5.5]dodecane-8-sulfonyl)-diazomethane, and
bis(1,4-dioxaspiro[4.5]decane-7-sulfonyl)diazomethane.

(6) Disulfonylmethane Compounds

As examples of disulfonylmethane compounds, a compound of the following formula (4) can be given:

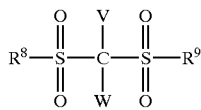

(4)

wherein $R^8$ and $R^9$ individually represent a linear or branched monovalent aliphatic hydrocarbon group, cycloalkyl group, aryl group, aralkyl group, or other monovalent organic group having a hetero atom, and V and W individually represent an aryl group, a hydrogen atom, a linear or branched monovalent aliphatic hydrocarbon group, or a monovalent organic group having a hetero atom, provided that at least one of V and W represents an aryl group, or V and W bond to form a mono-carbocyclic or poly-carbocyclic structure having at least one unsaturated bond, or V and W bond to form a group of the following formula:

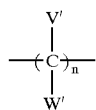

wherein V' and W' individually represent a hydrogen atom, halogen atom, linear or branched alkyl group, cycloalkyl group, aryl group, or aralkyl group, or V' and W', each bonding to the same or different carbon atoms, bond to form a mono-carbocyclic structure, and n is an integer of 2–10.

(7) Oxime Sulfonate Compounds

As examples of oxime sulfonate compounds, compounds of the following formula (5) or (6) can be given:

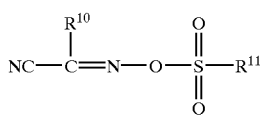

(5)

wherein $R^{10}$ and $R^{11}$ individually represent a monovalent organic group,

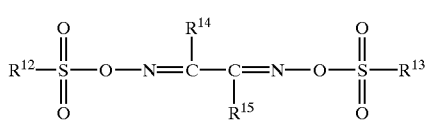

(6)

wherein $R^{12}$, $R^{13}$, $R^{14}$, and $R^{15}$ individually represent a monovalent organic group.

As specific preferable examples of $R^{10}$ in the formula (5), a methyl group, ethyl group, n-propyl group, phenyl group, tosyl group, trifluoromethyl group, and pentafluoroethyl group can be given. As preferable examples of $R^{11}$, a phenyl group, tosyl group, and 1-naphthyl group can be given.

As specific preferable examples of $R^{12}$ and $R^{13}$ in the formula (6), a methyl group, ethyl group, n-propyl group, phenyl group, tosyl group, trifluoromethyl group, and pentafluoroethyl group can be given. As preferable examples of $R^{14}$ and $R^{15}$, a phenyl group, tosyl group, and 1-naphthyl group can be given.

(8) Hydrazine Sulfonate Compounds:

As specific examples of hydrazine sulfonate compounds, bis(benzenesulfonyl)hydrazine, bis(p-toluenesulfonyl)hydrazine, bis(trifluoromethanesulfonyl)hydrazine, bis(pentafluoroethanesulfonyl)hydrazine, bis(n-propanesulfonyl)hydrazine, benzenesulfonylhydrazine, p-toluenesulfonylhydrazine, trifluoromethafnesulfonylhydrazine, pentafluoroethanesulfonylhydrazine, n-propanesulfonylhydrazine, and trifluoromethanesulfonylp·toluenesulfonylhydrazine can be given.

The acid generator (C) can be used either individually or in combination of two or more in the chemically amplified radiation sensitive resin composition [I].

The amount of the acid generator (C) used is preferably 0.1–20 parts by weight, and still more preferably 0.5–15 parts by weight, for 100 parts by weight of the acid-dissociable group-containing resin (B).

Acid Diffusion Controller

It is preferable to add an acid diffusion controller to the chemically amplified radiation sensitive resin composition [I]. The acid diffusion controller controls diffusion of an acid generated from the acid generator (C) upon exposure in the resist film to hinder unfavorable chemical reactions in the unexposed area.

The addition of the acid diffusion controller improves storage stability of the composition and resolution as a resist. Moreover, the addition of the acid diffusion controller prevents the line width of the resist pattern from changing due to variation of post-exposure delay (PED) from exposure to post-exposure heat treatment, whereby a composition with remarkably superior process stability can be obtained.

As the acid diffusion controller, organic compounds containing nitrogen of which the basicity does not change during exposure or heating for forming a resist pattern are preferable.

As examples of such nitrogen-containing organic compounds, a compound shown by the following formula (7) (hereinafter called "nitrogen-containing compound (α)"),

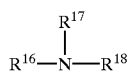

(7)

wherein $R^{16}$, $R^{17}$, and $R^{18}$ individually represent a hydrogen atom, a substituted or unsubstituted alkyl group, substituted or unsubstituted aryl group, or substituted or unsubstituted aralkyl group, a diamino compound having two nitrogen atoms in the molecule (hereinafter referred to as "nitrogen-containing compound (β)"), a diamino polymer having three or more nitrogen atoms in the molecule (hereinafter referred to as "nitrogen-containing compound (γ)") an amide group-containing compound, urea compound, and nitrogen-containing heterocyclic compound can be given.

As examples of the nitrogen-containing compounds (α), linear, branched, or cyclicmonoalkylamines such as n-hexylamine, n-heptylamine, n-octylamine, n-nonylamine, n-decylamine, and cyclohexylamine; dialkylamines such as di-n-butylamine, di-n-pentylamine, di-n-hexylamine, di-n-heptylamine, di-n-octylamine, di-n-nonylamine, di-n-decylamine, methyl·cyclohexylamine, and dicyclohexylamine; linear, branched, or cyclic trialkylamines such as triethylamine, tri-n-propylamine, tri-n-butylamine, tri-n- pentylamine, tri-n-hexylamine, tri-n-heptylamine, tri-n-octylamine, tri-n-nonylamine, tri-n-decylamine, cyclohexyldimethylamine, methyldicyclohexylamine, and tricyclohexylamine; and aromatic amines such as aniline, N-methylaniline, N,N-dimethylaniline, 2-methylaniline, 3-methylaniline, 4-methylaniline, 4-nitroaniline, diphenylamine, triphenylamine, and naphthylamine can be given.

Examples of the nitrogen-containing compounds (β) include ethylenediamine, N,N,N',N'-tetramethylethylenediamine, N,N,N',N'-tetrakis(2-hydroxypropyl)ethylenediamine, tetramethylenediamine, hexamethylenediamine, 4,4'-diaminodiphenylmethane, 4,4'-diaminodiphenyl ether, 4,4'-diaminobenzophenone, 4,4'-diaminodiphenylamine, 2,2'-bis(4-aminophenyl)propane, 2-(3-aminophenyl)-2-(4-aminophenyl)propane, 2-(4-aminophenyl)-2-(3-hydroxyphenyl)propane, 2-(4-aminophenyl)-2-(4-hydroxyphenyl)propane, 1,4-bis[1-(4-aminophenyl)-1-methylethyl]benzene, and 1,3-bis[1-(4-aminophenyl)-1-methylethyl]benzene.

Examples of the nitrogen-containing compounds (γ) include polyethyleneimine, polyallylamine, and a polymer of N-(dimethylaminoethyl)acrylamide.

Examples of compounds containing an amide group include formamide, N-methylformamide, N,N-dimethylformamide, acetamide, N-methylacetamide, N,N-dimethylacetamide, propionamide, benzamide, pyrrolidone, and N-methylpyrrolidone.

Examples of urea compounds include urea, methylurea, 1,1-dimethylurea, 1,3-dimethylurea, 1,1,3,3-tetramethylurea, 1,3-diphenylurea, and tributylthiourea.

Examples of the nitrogen-containing heterocyclic compounds include imidazoles such as imidazole, benzimidazole, 4-methylimidazole, 4-methyl-2-phenylimidazole, and 2-phenylbenzimidazole; pyridines such as pyridine, 2-methylpyridine, 4-methylpyridine, 2-ethylpyridine, 4-ethylpyridine, 2-phenylpyridine, 4-phenylpyridine, 2-methyl-4-phenylpyridine, nicotine, nicotinic acid, nicotinamide, quinoline, 8-oxyquinoline, and acridine; pyrazine, pyrazole, pyridazine, quinoxaline, purine, pyrrolidine, piperidine, morpholine, 4-methylmorpholine, piperazine, 1,4-dimethylpiperazine, and 1,4-diazabicyclo[2.2.2]octane.

Base precursors possessing an acid-dissociable group, such as N-(t-butoxycarbonyl)piperidine,
N-(t-butoxycarbonyl)imidazole,
N-(t-buoxycarbonyl)benzimidazole,
N-(t-butoxycarbonyl)-2-phenylbenzimidazole,
N-(t-butoxycarbonyl)di-n-octylamine, N-(t-butoxy carbonyl)diethanolamine,
N-(t-butoxycarbonyl)dicyclohexylamine, and
N-(t-butoxycarbonyl)diphenylamine can be used as nitrogen-containing organic compounds acting as an acid diffusion controller.

Of these nitrogen-containing organic compounds, the nitrogen-containing compound (α) and the nitrogen-containing heterocyclic compound are preferable. Trialkylamines are particularly preferable among the nitrogen-containing compound (α), and pyridines are particularly preferable among the nitrogen-containing heterocyclic compounds.

The acid diffusion controller may be used either individually or in combination of two or more.

The amount of the acid diffusion controller to be added is usually 15 parts by weight or less, preferably 0.001–10 parts by weight, and still more preferably 0.005–5 parts by weight for 100 parts by weight of the acid-dissociable group-containing resin (B). If the proportion of the acid diffusion controller exceeds 15 parts by weight, sensitivity as a resist and developability of the exposed area tend to decrease. If the proportion is less than 0.001 part by weight, accuracy of pattern profiles and dimensions as a resist may decrease depending on processing conditions.

Surfactant

Surfactants exhibiting an action of improving the applicability or striation of the composition and developability as a resist may be added to the radiation-sensitive resin composition [I].

Examples of such surfactants include polyoxyethylene lauryl ether, polyoxyethylene stearyl ether, polyoxyethylene oleyl ether, polyoxyethylene n-octyl phenol ether, polyoxyethylene n-nonyl phenol ether, polyethylene glycol dilaurate, polyethylene glycol distearate; and commercially available products such as FTOPEF301, EF303, EF352 (manufactured by TOHKEM PRODUCTS CORPORATION), MEGAFAC F171, F173 (manufactured by Dainippon Ink and Chemicals, Inc.), Fluorad FC430, FC431 (manufactured by Sumitomo 3M Ltd.), Asahi Guard AG710, Surflon S-382, SC-101, SC-102, SC-103, SC-104, SC-105, SC-106 (manufactured by Asahi Glass Co., Ltd.), KP341 (manufactured by Shin-Etsu Chemical Co., Ltd.), and Polyflow No. 75, No. 95 (manufactured by Kyoeisha Chemical Co., Ltd.)

These surfactants may be used either individually or in combination of two or more. The amount of the surfactants to be added is usually 2 parts by weight or less for 100 parts by weight of the acid-dissociable group-containing resin (B).

Other sensitizer

Sensitizers other than the carbazole derivative (1) can be added to the composition of the present invention (such sensitizers are hereinafter referred to as "other acid sensitizers").

As preferable examples of the other sensitizers, benzophenones, rose bengals, and anthracenes can be given.

These other sensitizers may be used either individually or in combination of two or more. The amount of the other sensitizers to be added is usually 50 parts by weight or less for 100 parts by weight of the acid-dissociable group-containing resin (B).

Other Additives

A dye and/or a pigment may be added to visualize latent images of exposed areas and to reduce the effect of halation during exposure. An adhesion adjuvant may be added to improve adhesiveness to the substrate.

Halation inhibitors such as 4-hydroxy-4'-methylchalcone, form improvers, preservation stabilizers, antifoaming agents, and the like can also be added.

Solvent

When used, the radiation-sensitive resin composition [1] is usually prepared into a composition solution by homogeneously dissolving the composition in a solvent so that the total solid concentration is 0.1–50 wt %, and preferably 1–40 wt %, and filtering the solution using a filter with a pore diameter of about 0.2 μm.

As examples of a solvent used for preparing the above composition solution, ethylene glycol monoalkyl ether acetates such as ethylene glycol monomethyl ether acetate, ethylene glycol monoethyl ether acetate, ethylene glycol mono-n-propyl ether acetate, and ethylene glycol mono-n-butyl ether acetate; propylene glycol monoalkyl ethers such as propylene glycol monomethyl ether, propylene glycol monoethyl ether, propylene glycol mono-n-propyl ether, and propylene glycol mono-n-butyl ether; propylene glycol dialkyl ethers such as propylene glycol dimethyl ether, propylene glycol diethyl ether, propylene glycol di-n-propyl ether, and propylene glycol di-n-butyl ether; propylene glycol monoalkyl ether acetates such as propylene glycol monomethyl ether acetate, propylene glycol monoethyl ether acetate, propylene glycol mono-n-propyl ether acetate, and propylene glycol mono-n-butyl ether acetate; lactic acid esters such as methyl lactate, ethyl lactate, n-propyl lactate, and i-propyl lactate; aliphatic carboxylic acid esters such as n-amyl formate, i-amyl formate, ethyl acetate, n-propyl acetate, i-propyl acetate, n-butyl acetate, 1-butyl acetate, n-amyl acetate, i-amyl acetate, i-propyl propionate, n-butyl propionate, and i-butyl propionate; other esters such as ethyl hydroxyacetate, ethyl 2-hydroxy-2-methylpropionate, methyl 2-hydroxy-3-methylbutyrate, ethyl methoxyacetate, ethyl ethoxyacetate, methyl 3-methoxypropionate, ethyl 3-methoxypropionate, methyl 3-ethoxypropionate, ethyl 3-ethoxypropionate, butyl 3-methoxyacetate, butyl 3-methyl-3-methoxyacetate, butyl 3-methyl-3-methoxypropionate, butyl 3-methyl-3-methoxybutyrate, methyl acetoacetate, ethyl acetoacetate, methyl pyruvate, and ethyl pyruvate; aromatic hydrocarbons such as toluene and xylene; ketones such as methyl ethyl ketone, 2-pentanone, 2-hexanone, 2-heptanone, 3-heptanone, 4-heptanone, and cyclohexanone; amides such as N-methylformamide, N,N-dimethylformamide, N-methylacetamide, N,N-dimethyl acetamide, and N-methylpyrrolidone; and lactones such as y-butyrolactone can be given.

These solvents may be used either individually or in combinations of two or more.

Formation of Resist Pattern

A resist pattern is formed from the radiation-sensitive resin composition [I] by applying the composition solution prepared as mentioned above to substrates such as a silicon wafer or a wafer covered with aluminum using an appropriate application method such as rotational coating, cast coating, and roll coating to form a resist film. The resist film is then optionally heated at a temperature of about 70–160° C. (hereinafter referred to as "PB") and exposed to light through a predetermined mask pattern.

Radiation used here can be appropriately selected according to the types of acid generator (C) from among deep ultraviolet rays such as a KrF excimer laser (wavelength: 248 nm), ArF excimer laser (wavelength: 193 nm), or $F_2$ excimer laser (wavelength: 157 nm), X-rays such as synchrotron radiation, and charged particle rays such as electron beams.

The exposure conditions such as the amount of exposure are appropriately determined depending on the composition of the radiation-sensitive resin composition [I], types of additives, and the like.

In the present invention, it is preferable to perform post-exposure bake (hereinafter referred to as "PEB") at 70–160° C. for 30 seconds or more in order to steadily form a minute resist pattern with high precision. If the heating temperature for PEB is less than 70° C., sensitivity may fluctuate according to the type of substrates.

A desired resist pattern is obtained by developing the resist using an alkaline developer at 10–50° C. for 10–200 seconds, preferably at 15–30° C. for 15–100 seconds, and still more preferably at 20–25° C. for 15–90 seconds.

As the alkaline developer, an alkaline aqueous solution prepared by dissolving an alkali such as an alkali metal hydroxide, aqueous ammonia, mono-, di-, or tri-alkylamine, mono-, di-, or tri-alkanclamine, heterocyclic amine, tetraalkylammonium hydroxide, choline, 1,8-diazabicyclo [5.4.0]-7-undecene, or 1,5-diazabicyclo[4.3.0]-5-nonene to a concentration of 1–10 wt %, preferably 1–5 wt %, and particularly preferably 1–3 wt % can be used.

Moreover, an appropriate amount of a water-soluble organic solvent such as methanol and ethanol or a surfactant can be added to the developer comprising the above alkaline aqueous solution.

When forming a resist pattern, a protective film may be provided on the resist film in order to prevent an adverse effect of basic impurities and the like which are present in the environmental atmosphere.

EXAMPLES

The embodiments of the present invention are described in more detail by examples. However, these examples should not be construed as limiting the present invention.

<Synthesis of Carbazole Derivative (1)>

Synthesis Example 1

100 g of carbazole, 83 g of bromoacetic acid, and 134 g of t-butoxy potassium were reacted in 1,000 g of dimethylformamide overnight at room temperature. After the addition of 300 g of 5 wt % oxalic acid aqueous solution, the reaction mixture was extracted with n-hexane. Precipitate obtained by crystallization in a mixed solvent of dimethylformamide and n-hexane was dried under vacuum to obtain 56 g of carbazole derivative (1) of the formula (1-1) as a white solid.

This compound is referred to as a "carbazole derivative (1) (A-1)".

Synthesis Example 2

100 g of carbazole, 117 g of t-butyl bromoacetate, and 67 g of t-butoxy potassium were reacted in 1,000 g of dimethylformamide overnight at room temperature. The reaction mixture was processed in the same manner as in the Synthesis Example 1 to obtain 79 g of carbazole derivative (1) of formula (1–7) as a white solid.

Figure 2:
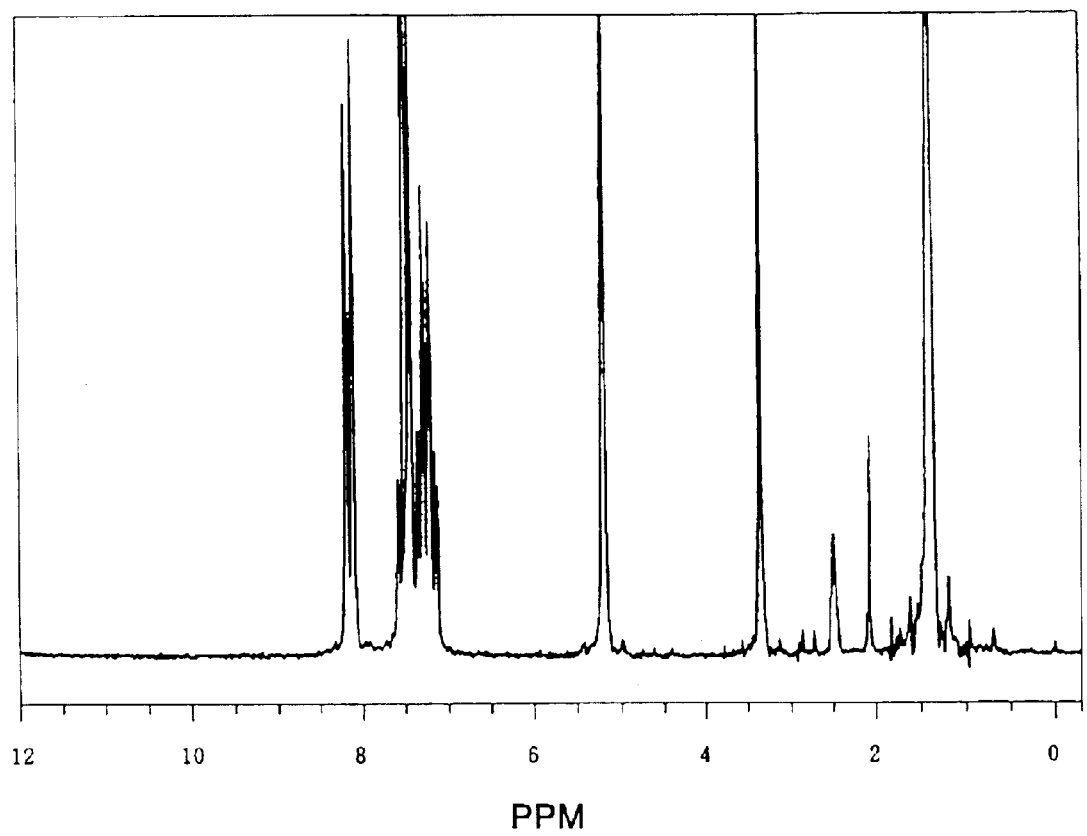
FIG. 2 is a $^1$H-NMR spectrum of the carbazole derivative (1) prepared in Synthetic Example 2.
Figure 3:
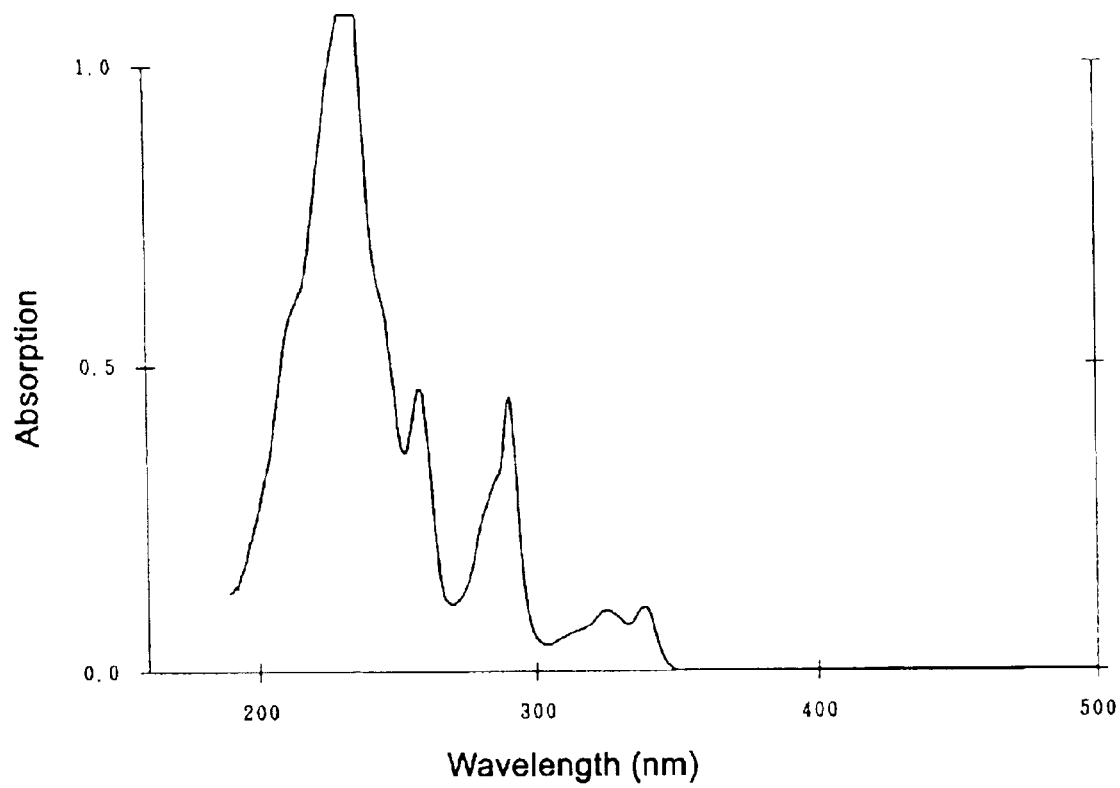
FIG. 3 is a UV absorption spectrum of the carbazole derivative (1) prepared in Synthetic Example 2.

IR absorption spectrum and $^1$H-NMR spectrum of this compound are respectively shown in FIG. 1 and FIG. 2. The UV absorption spectrum of this compound was measured and shown in FIG. 3. The UV absorption spectrum indicates a particularly strong absorption around the wavelength of 200–250 nm.

This compound is referred to as a "carbazole derivative (1) (A-2)".

Synthesis Example 3

100 g of carbazole, 137 g of benzyl bromoacetate, and 67 g of t-butoxy potassium were reacted in 1,000 g of dimethylformamide overnight at room temperature. The reaction mixture was processed in the same manner as in the Synthesis Example 1 to obtain 85 g of carbazole derivative (1) of the formula (1-10) as a white solid.

This compound is referred to as a "carbazole derivative (1) (A-3)".

Synthesis Example 4

100 g of carbazole, 108 g of i-propyl bromoacetate, and 67 g of t-butoxy potassium were reacted in 1,000 g of dimethylformamide overnight at room temperature. The reaction mixture was processed in the same manner as in the Synthesis Example 1 to obtain 62 g of carbazole derivative (1) of the formula (1-6) as a white solid.

This compound is referred to as a "carbazole derivative (1) (A-4)".

Synthesis Example 5

100 g of carbazole, 132 g of cyclohexyl bromoacetate, and 67 g of t-butoxy potassium were reacted in 1,000 g of dimethylformamide overnight at room temperature. The reaction mixture was processed in the same manner as in the Synthesis Example 1 to obtain 99 g of carbazole derivative (1) of the formula (1-8) as a white solid.

This compound is referred to as a "carbazole derivative (1) (A-5)".

Synthesis Example 6

100 g of carbazole, 125 g of t-butyl 2-bromopropionate, and 67 g of t-butoxy potassium were reacted in 1,000 g of dimethylformamide overnight at room temperature. The reaction mixture was processed in the same manner as in the Synthesis Example 1 to obtain 85 g of carbazole derivative (1) of the formula (1-20) as a white solid.

This compound is referred to as a "carbazole derivative (1) (A-6)".

Synthesis Example 7

100 g of carbazole, 149 g of cyclohexyl 2-bromoisobutyrate, and 67 g of t-butoxy potassium were reacted in 1,000 g of dimethylformamide overnight at room temperature. The reaction mixture was processed in the same manner as in the Synthesis Example 1 to obtain 105 g of carbazole derivative (1) of the formula (1-34) as a white solid.

This compound is referred to as a "carbazole derivative (1) (A-7)".

Synthesis Example 8

100 g of carbazole, 173 g of cyclohexyl α-bromocyclohexanecarboxylate, and 67 g of t-butoxy potassium were reacted in 1,000 g of dimethylformamide overnight at room temperature. The reaction mixture was processed in the same manner as in the Synthesis Example 1 to obtain 105 g of carbazole derivative (1) of the formula (1-73) as a white solid.

This compound is referred to as a "carbazole derivative (1) (A-8)".

<Preparation of Acid-dissociable Group-Containing Resin (B)>

Mw and Mn of the resins prepared in Synthesis Examples 9–18 were measured by gel permeation chromatography (GPC) using GPC columns (manufactured by Tosoh Corp., G2000H$_{XL}$×2, G3000H$^{XL}$×1, G4000H$_{XL}$×1) under the following conditions. Flow rate: 1.0 ml/minute, eluate: tetrahydrofuran, column temperature: 40° C., standard reference material: monodispersed polystyrene Synthesis Example 9

101 g of p-acetoxystyrene, 5 g of styrene, 42 g of p-t-butoxystyrene, 6 g of azobisisobutyronitrile, and 1 g of t-dodecylmercaptan were dissolved in 160 g of propylene glycol monomethyl ether. The mixture was polymerized at 70° C. for 16 hours in a nitrogen atmosphere. After the polymerization, the reaction solution was added dropwise to a large quantity of n-hexane to coagulate and purify the resulting resin.

After the addition of 150 g of propylene glycol monomethyl ether to the resin, 300 g of methanol, 80 g of triethylamine, and 15 g of distilled water were added. The mixture was hydrolyzed for 8 hours while refluxing at the boiling point. After the reaction, the solvent and triethylamine were evaporated under reduced pressure. The resulting resin was dissolved in acetone and added dropwise to a large quantity of distilled water to coagulate the resin. The resulting white powder was filtered and dried overnight at 50° C. under reduced pressure.

The resin was found to have Mw and Mw/Mn of 16,000 and 1.7 respectively. The result of $^{13}$C-NMR analysis confirmed that the resin was a copolymer of p-hydroxystyrene, styrene, and p-t-butoxystyrene at a copolymerization molar ratio of 72:5:23.

This resin is referred to as "acid-dissociable group-containing resin (B-1)".

Synthesis Example 10

100 g of p-acetoxystyrene, 25 g of t-butyl acrylate, 18 g of styrene, 6 g of azobisisobutyronitrile, and 1 g of t-dodecylmercaptan were dissolved in 230 g of propylene glycol monomethyl ether. The mixture was polymerized at 70° C. for 16 hours in a nitrogen atmosphere. After the polymerization, the reaction solution was added dropwise to a large quantity of n-hexane to coagulate and purify the resulting resin.

After the addition of 150 g of propylene glycol monomethyl ether to the resin, 300 g of methanol, 80 g of triethylamine, and 15 g of distilled water were added. The mixture was hydrolyzed for 8 hours while refluxing at the boiling point. After the reaction, the solvent and triethylamine were evaporated under reduced pressure. The resulting resin was dissolved in acetone and added dropwise to a large quantity of distilled water to coagulate the resin. The resulting white powder was filtered and dried overnight at 50° C. under reduced pressure.

The resin was found to have Mw and Mw/Mn of 11,500 and 1.6 respectively. The result of $^{13}$C-NMR analysis confirmed that the resin was a copolymer of p-hydroxystyrene, t-butyl acrylate, and styrene at a copolymerization molar ratio of 61:19:20.

This resin is referred to as "acid-dissociable group-containing resin (B-2)".

Synthesis Example 11

125 g of p-acetoxystyrene, 20 g of t-butyl acrylate, 10 g of styrene, 8 g of 2,5-dimethylhexane-2,5-diacrylate, 8 g of azobisisobutyronitrile, and 6 g of t-dodecylmercaptan were dissolved in 170 g of propylene glycol monomethyl ether. The mixture was polymerized for 16 hours at 70° C. in a nitrogen atmosphere. After the polymerization, the reaction solution was added dropwise to a large quantity of n-hexane to coagulate and purify the resulting resin.

After the addition of 150 g of propylene glycol monomethyl ether to the resin, 300 g of methanol, 80 g of triethylamine, and 15 g of distilled water were added. The mixture was hydrolyzed for 8 hours while refluxing at the boiling point. After the reaction, the solvent and triethylamine were evaporated under reduced pressure. The resulting resin was dissolved in acetone and added dropwise to a large quantity of distilled water to coagulate the resin. The resulting white powder was filtered and dried overnight at 50° C. under reduced pressure.

The resin was found to have Mw and Mw/Mn of 40,000 and 2.6, respectively. The result of $^{13}$C-NMR analysis confirmed that the resin was a copolymer of p-hydroxystyrene, t-butyl acrylate, styrene, and 2,5-dimethylhexane-2,5-diacrylate at a copolymerization molar ratio of 72:10:15:3.

This resin is referred to as "acid-dissociable group-containing resin (B-3)".

Synthesis Example 12

140 g of p-acetoxystyrene, 50 g of p-t-butoxystyrene, 9 g of 2,5-dimethylhexane-2,5-diacrylate, 8 g of azobisisobutyronitrile, and 6 g of t-dodecylmercaptan were dissolved in 240 g of propylene glycol monomethyl ether. The mixture was polymerized for 16 hours at 70° C. in a nitrogen atmosphere. After the polymerization, the reaction solution was added dropwise to a large quantity of n-hexane to coagulate and purify the resulting resin.

After the addition of 150 g of propylene glycol monomethyl ether to the resin, 300 g of methanol, 100 g of triethylamine, and 15 g of distilled water were added. The mixture was hydrolyzed for 8 hours while refluxing at the boiling point. After the reaction, the solvent and triethylamine were evaporated under reduced pressure. The resulting resin was dissolved in acetone and added dropwise to a large quantity of distilled water to coagulate the resin. The resulting white powder was filtered and dried overnight at 50° C. under reduced pressure.

The resin was found to have Mw and Mw/Mn of 40,000 and 2.6, respectively. The result of $^{13}$C-NMR analysis confirmed that the resin was a copolymer of p-hydroxystyrene, p-t-butoxystyrene, and 2,5-dimethylhexane-2,5-diacrylate at a copolymerization molar ratio of 67:30:3.

This resin is referred to as "acid-dissociable group-containing resin (B-4)".

Synthesis Example 13

176 g of p-t-butoxystyrene was anionically polymerized at −78° C. in 500 ml of tetrahydrofuran using n-butyllithium as a catalyst. The reaction solution was added dropwise to methanol to coagulate, thereby obtaining 150 g of poly(p-t-butoxystyrene) as a white solid.

The poly(p-t-butoxystyrene) was dissolved in 600 g of dioxane. After the addition of diluted hydrochloric acid, the mixture was hydrolyzed at 70° C. for 2 hours. The reaction product was caused to coagulate by adding to a large quantity of distilled water, thereby obtaining a white resin. Then, a step of dissolving the resulting resin in acetone and adding the solution dropwise to a large quantity of distilled water to coagulate the resin was repeated. The resulting white powder was filtered and dried overnight at 50° C. under reduced pressure.

The Mw and Mw/Mn of this resin were 10,400 and 1.10, respectively. $^{13}$C-NMR analysis confirmed that the resin is a copolymer of p-t-butoxystyrene and p-hydroxystyrene at a copolymerization molar ratio of these monomers of 68:32, in which part of t-butyl group in the poly(p-t-butoxystyrene) had a hydrolyzed structure.

This resin is referred to as "acid-dissociable group-containing resin (B-5)".

Synthesis Example 14

7 g of di-t-butyl carbonate was added to a solution in which 12 g of poly(p-hydroxystyrene) with Mw of 8,000 and 5 g of triethylamine were dissolved in 50 g of dioxane while stirring. The mixture was stirred for 6 hours at room temperature. An aqueous solution of 3 wt % oxalic acid was then added to neutralize triethylamine. The reaction solution was dropped into a large quantity of distilled water to coagulate the resin. The coagulated resin was washed with distilled water several times. The resin was then filtered and dried at 50° C. overnight under reduced pressure.

Mw and Mw/Mn of this resin were respectively 9,200 and 1.8. As a result of $^{13}$C-NMR analysis, the resin was found to have a structure in which 30 mol % of hydrogen atoms of a phenolic hydroxyl group in poly(p-hydroxystyrene) was replaced by t-butoxycarbonyl groups.

This resin is referred to as "acid-dissociable group-containing resin (B-6)".

Synthesis Example 15

24 g of poly(p-hydroxystyrene) with Mw of 12,000 was dissolved in 100 g of dioxane. Nitrogen gas was bubbled through the mixture for 30 minutes. After the addition of 3 g of ethyl vinyl ether, 3 g of ethyl 1-propenyl ether, and 1 g of pyridinium p-toluenesulfonate as a catalyst, the mixture was reacted for 12 hours at room temperature. The reaction solution was dropped into a large quantity of 1 wt % ammonium aqueous solution to coagulate the resin. The coagulated resin was filtered and dried overnight at 50° C. under reduced pressure.

Mw and Mw/Mn of this resin were respectively 15,000 and 1.6. As a result of $^{13}$C-NMR analysis, the resin was found to have a structure in which 20 mol % of hydrogen atoms of a phenolic hydroxyl group in poly(p-hydroxystyrene) was replaced by 1-ethoxyethyl groups, and 15 mol % by 1-ethoxy propyl groups.

This resin is referred to as "acid-dissociable group-containing resin (B-7)".

Synthesis Example 16

20 g of di-t-butyl carbonate was added to a solution in which 120 g of poly(p-hydroxystyrene) with Mw of 12,000 and 15 g of triethylamine were dissolved in 500 g of dioxane while stirring. The mixture was stirred for 6 hours at room temperature. An aqueous solution of 3 wt % oxalic acid was then added to neutralize triethylamine. The reaction solution was dropped into a large quantity of distilled water to coagulate the resin. The coagulated resin was washed with distilled water several times. The resin was then filtered and dried at 50° C. overnight under reduced pressure.

Mw and Mw/Mn of this resin were respectively 8,900 and 2.8. As a result of $^{13}$C-NMR analysis, the resin was found to have a structure in which 9 mol % of hydrogen atoms of a phenolic hydroxyl group in poly(p-hydroxystyrene) was replaced by t-butoxycarbonyl groups.

This resin was dissolved in 100 g of dioxane and nitrogen gas was bubbled through the solution for 30 minutes. After the addition of 2 g of ethyl vinyl ether, 2 g of ethyl-1-propenyl ether, and 1 g of pyridinium p-toluenesulfonate as a catalyst, the mixture was reacted for 12 hours at room temperature. The reaction solution was dropped into a large quantity of 1 wt % ammonium aqueous solution to coagulate the resin. The coagulated resin was filtered and dried overnight at 50° C. under reduced pressure.

Mw and Mw/Mn of this resin were respectively 11,000 and 2.8. As a result of $^{13}$C-NMR analysis, the resin was found to have a structure in which 14 mol % of hydrogen atoms of the phenolic hydroxyl group in poly(p-hydroxystyrene) was replaced by 1-ethoxyethyl groups, 11 mol % by 1-ethoxy propyl groups, and 9 mol % by t-butoxycarbonyl groups.

This resin is referred to as "acid-dissociable group-containing resin (B-8)".

Synthesis Example 17

25 g of a copolymer of p-hydroxystyrene and p-t-butoxystyrene with a copolymerization of molar ratio of these monomers of 90:10 was dissolved in 100 g of n-butyl acetate. Nitrogen gas was bubbled through the solution for 30 minutes. After the addition of 3.3 g of ethyl vinyl ether and 1 g of pyridinium p-toluenesulfonate as a catalyst, the mixture was reacted at room temperature for 12 hours. The reaction solution was dropped into a large quantity of 1 wt % ammonium aqueous solution to coagulate the resin. The coagulated resin was filtered and dried overnight at 50° C. under reduced pressure.

Mw and Mw/Mn of this resin were respectively 13,000 and 1.01. As a result of $^{13}$C-NMR analysis, the resin was found to have a structure in which 23 mol % of hydrogen atoms of the phenolic hydroxyl group in poly(p-hydroxystyrene) was replaced by ethoxyethyl groups, and 10 mol % by t-butyl groups.

This resin is referred to as "acid-dissociable group-containing resin (B-9)".

Synthesis Example 18

114 g of p-acetoxystyrene, 19 g of t-butyl acrylate, 32 g of p-t-butoxystyrene, 6 g of azobisisobutyronitrile, and 1 g of t-dodecylmercaptan were dissolved in 230 g of propylene glycol monomethyl ether. The mixture was polymerized at 70° C. for 16 hours in a nitrogen atmosphere. After the polymerization, the reaction solution was added dropwise to a large quantity of n-hexane to coagulate and purify the resulting resin.

After the addition of 150 g of propylene glycol monomethyl ether to the resin, 300 g of methanol, 80 g of triethylamine, and 15 g of distilled water were added. The mixture was hydrolyzed for 8 hours while refluxing at the boiling point. After the reaction, the solvent and triethylamine were evaporated under reduced pressure. The resulting resin was dissolved in acetone and added dropwise to a large quantity of distilled water to coagulate the resin. The resulting white powder was filtered and dried overnight at 50° C. under reduced pressure.

The resin was found to have Mw and Mw/Mn of 11,500 and 1.6 respectively. The result of $^{13}$C-NMR analysis confirmed that the resin was a copolymer of p-hydroxystyrene, t-butyl acrylate, and p-t-butoxystyrene at a copolymerization molar ratio of 65:15:20.

This resin is referred to as "acid-dissociable group-containing resin (B-10)".

<Chemically Amplified Radiation-sensitive Resin Composition>

Examples 1–21 and Comparative Examples 1–2

Components shown in Table 1 were mixed to prepare homogeneous solutions. The solutions were filtered through a membrane filter with a pore diameter of 0.2 μm to prepare solution compositions.

The solution composition was spin-coated on a silicon wafer substrate. PB was then performed under the conditions shown in Table 3 to form resist coatings with a thickness of 0.5 μm from the compositions of Examples 1–17, Examples 19–21, and Comparative Examples 1–2, and a resist coating with a thickness of 0.1 μm from the composition of Example 18.

The resist coatings were exposed to radiations using a stepper "NSR2205 EX12B" (manufactured by Nikon Corp., numerical aperture: 0.55) in Examples 1–17 and Comparative Examples 1–2, an $F_2$ excimer laser exposure apparatus "XLS" (manufactured by Ultratech Corp., numerical aperture: 0.60) in Examples 18, and an electron beam lithography system "HL700" (manufactured by Hitachi, Ltd., acceleration voltage: 30 KeV) in which the acceleration voltage was remodeled to 50 KeV. PEB was the performed under the conditions shown in Table 2.

The resist coatings were developed at 23° C. for 1 minute by a paddle method using a 2.38 wt % tetramethylammonium hydroxide aqueous solution. The resist coatings were then washed with purified-water and dried to form a resist pattern.

The results of the evaluation of each resist are shown in Table 3.

Evaluation of resists was carried out as follows.
Sensitivity:

Sensitivity was evaluated based on an optimum exposure dose which is a dose capable of forming a 1:1 line and space pattern (1L1S) with a line width of 0.22 μm, when a resist coating formed on a silicon wafer substrate is exposed to light, immediately followed by PEB, development, washing with water, and drying.
Resolution:

The minimum line and space (1L1S) dimension resolved by an optimum does of irradiation was taken as the resolution.
Pattern Profile:

The cross-section of a line-and-space (1L1S) pattern with a line width of 0.22 μm was measured by a scanning electron microscope. The pattern profile was evaluated according to the following standard, wherein La and Lb respectively indicate the line width at the top and bottom of the pattern cross-section.

Good: 0.9<La/Lb<1.1

Bad: 0.9 2≧La/Lb or La/Lb≧1.1
PED Stability:

A line and space pattern (1L1S) with a designed line width of 0.26 μm was prepared in the same manner as the above resist patterns, except that PEB was performed after leaving the substrate after the exposure processing in a chamber in which the ammonia concentration was controlled to 5 ppb. The PED stability was evaluated according to the following standard, wherein La indicates the line width at the top of the pattern.

Good: 0.85×0.26 μm<La<1.1×0.26 μm

Bad: La≦0.85×0.26 μm or La≦1.1×0.26 μm
Storage Stability:

The sensitivity, resolution, and pattern profile were evaluated using the radiation-sensitive resin compositions stored at 23° C. for 6 months after preparation. The compositions showing the same evaluation results as those as prepared, and exhibiting no development defects, and producing no foreign matters after storage were deemed to have "Good" storage stability.

The acid generators (C), acid diffusion controllers, other additives, and solvents in Table 1 are as follows.
Acid Generator (C)

C-1: bis(4-t-butylphenyl)iodonium nonafluoro-n-butanesulfonate

C-2: bis(4-t-butylphenyl)iodonium 10-camphorsulfonate

C-3: bis(4-t-butylphenyl)iodoniumtrifluoromethane sulfonate

C-4: N-(trifluoromethanesulfonyloxy)bicyclo[2.2.1]hept-5-ene-2,3-dicarboxyimide
C-5: bis(cyclohexanesulfonyl)diazomethane
C-6: triphenylsulfonium trifluoromethanesulfonate
C-7; N-(10-camphorsulfonyloxy)succinimide Acid Diffusion Controller
D-1: tri-n-octylamine
D-2: triethanolamine
D-3: 2-phenylpyridine
D-4: N,N,N,N-tetrakis(2-hydroxypropyl)ethylenediamine
D-5: 2-phenylbenzimidazole Other Additives
E-1: 1-adamantane carboxylic acid Solvent
S-1: ethyl lactate
S-2: ethyl 3-ethoxypropionate
S-3: propylene glycol monomethyl ether acetate
S-4: 2-heptanone

TABLE 1

|  | Carbazole derivative (1) | Resin (B) | Acid generator (C) | Acid diffusion controller | Other additives | Solvent |
|---|---|---|---|---|---|---|
| Example 1 | A-1 (2) | B-1 (100) | C-4 (6) | D-5 (0.2) | — | S-1 (500) |
| Example 2 | A-2 (2) | B-1 (100) | C-4 (6) | D-5 (0.2) | — | S-1 (500) |
| Example 3 | A-2 (2) | B-2 (100) | C-2 (2) C-3 (2) | D-4 (0.2) | E-1 (0.1) | S-1 (500) |
| Example 4 | A-2 (2) | B-3 (100) | C-4 (3) C-7 (2) | D-2 (0.2) | — | S-1 (500) |
| Example 5 | A-2 (2) | B-4 (100) | C-4 (4) | D-3 (0.2) | — | S-1 (500) |
| Example 6 | A-2 (2) | B-5 (100) | C-2 (1) C-5 (5) | D-1 (0.2) | — | S-1 (350) S-3 (150) |
| Example 7 | A-2 (2) | B-6 (100) | C-5 (5) | D-2 (0.2) | — | S-1 (350) S-3 (150) |
| Example 8 | A-2 (2) | B-7 (100) | C-5 (5) | D-2 (0.2) | — | S-3 (500) |
| Example 9 | A-2 (2) | B-8 (100) | C-5 (4) C-2 (1) | D-2 (0.2) | — | S-1 (350) S-3 (150) |
| Example 10 | A-2 (2) | B-9 (100) | C-5 (5) | D-5 (0.2) | — | S-1 (500) |
| Example 11 | A-2 (2) | B-10 (100) | C-5 (5) | D-2 (0.2) | — | S-4 (500) |
| Example 12 | A-3 (2) | B-1 (100) | C-4 (4) | D-5 (0.2) | — | S-1 (350) S-2 (150) |
| Example 13 | A-4 (2) | B-1 (100) | C-4 (4) | D-5 (0.2) | — | S-1 (350) S-2 (150) |
| Example 14 | A-5 (2) | B-1 (100) | C-4 (4) | D-5 (0.1) | — | S-1 (350) S-2 (150) |
| Example 15 | A-6 (2) | B-1 (100) | C-4 (4) | D-5 (0.2) | — | S-1 (350) S-2 (150) |
| Example 16 | A-7 (2) | B-1 (100) | C-4 (4) | D-5 (0.2) | — | S-1 (500) |
| Example 17 | A-8 (2) | B-1 (100) | C-4 (4) | D-5 (0.2) | — | S-1 (500) |
| Example 18 | A-2 (2) | B-1 (100) | C-4 (4) | D-5 (0.1) | — | S-1 (500) |
| Example 19 | A-2 (2) | B-1 (100) | C-4 (5) | D-5 (0.1) | — | S-1 (500) |
| Example 20 | A-2 (2) | B-2 (100) | C-6 (3) | D-5 (0.1) | — | S-1 (500) |
| Example 21 | A-2 (2) | B-10 (100) | C-5 (5) | D-5 (0.1) | — | S-1 (500) |
| Comparative Example 1 | — | B-1 (100) | C-1 (2) C-3 (2) | D-4 (0.2) | E-1 (0.1) | S-1 (500) |
| Comparative Example 2 | — | B-1 (100) | C-1 (6) | D-4 (0.2) | E-1 (0.1) | S-1 (500) |

Unit in parenthesis: part by weight

TABLE 2

|  | PB | | | PEB | |
|---|---|---|---|---|---|
|  | Temp (° C.) | Time (sec) | Radiation | Temp (° C.) | Time (sec) |
| Example 1 | 130 | 60 | KrF excimer laser | 130 | 60 |
| Example 2 | 130 | 60 | KrF excimer laser | 130 | 60 |
| Example 3 | 130 | 60 | KrF excimer laser | 130 | 60 |
| Example 4 | 130 | 60 | KrF excimer laser | 130 | 60 |
| Example 5 | 130 | 60 | KrF excimer laser | 130 | 60 |
| Example 6 | 100 | 60 | KrF excimer laser | 100 | 60 |
| Example 7 | 90 | 60 | KrF excimer laser | 100 | 60 |
| Example 8 | 95 | 60 | KrF excimer laser | 100 | 60 |
| Example 9 | 100 | 60 | KrF excimer laser | 90 | 60 |
| Example 10 | 90 | 60 | KrF excimer laser | 90 | 60 |
| Example 11 | 80 | 60 | KrF excimer laser | 90 | 60 |
| Example 12 | 130 | 60 | KrF excimer laser | 120 | 60 |
| Example 13 | 120 | 60 | KrF excimer laser | 120 | 60 |
| Example 14 | 110 | 60 | KrF excimer laser | 130 | 60 |

TABLE 2-continued

| | PB | | | PEB | |
|---|---|---|---|---|---|
| | Temp (° C.) | Time (sec) | Radiation | Temp (° C.) | Time (sec) |
| Example 15 | 120 | 60 | KrF excimer laser | 130 | 60 |
| Example 16 | 130 | 60 | KrF excimer laser | 130 | 60 |
| Example 17 | 130 | 60 | KrF excimer laser | 130 | 60 |
| Example 18 | 130 | 60 | KrF excimer laser | 130 | 60 |
| Example 19 | 110 | 60 | Electronic beams | 130 | 60 |
| Example 20 | 110 | 60 | Electronic beams | 130 | 60 |
| Example 21 | 110 | 60 | Electronic beams | 130 | 60 |
| Comparative Example 1 | 130 | 60 | KrF excimer laser | 130 | 60 |
| Comparative Example 2 | 130 | 60 | KrF excimer laser | 130 | 60 |

TABLE 3

| | Sensitivity | Resolution ($\mu$m) | Pattern profile | PED Stability | Storage stability |
|---|---|---|---|---|---|
| Example 1 | 100 J/m$^2$ | 0.20 | Good | Good | Good |
| Example 2 | 120 J/m$^2$ | 0.21 | Good | Good | Good |
| Example 3 | 110 J/m$^2$ | 0.19 | Good | Good | Good |
| Example 4 | 130 J/m$^2$ | 0.18 | Good | Good | Good |
| Example 5 | 90 J/m$^2$ | 0.17 | Good | Good | Good |
| Example 6 | 100 J/m$^2$ | 0.19 | Good | Good | Good |
| Example 7 | 110 J/m$^2$ | 0.20 | Good | Good | Good |
| Example 8 | 100 J/m$^2$ | 0.20 | Good | Good | Good |
| Example 9 | 100 J/m$^2$ | 0.20 | Good | Good | Good |
| Example 10 | 110 J/m$^2$ | 0.20 | Good | Good | Good |
| Example 11 | 90 J/m$^2$ | 0.20 | Good | Good | Good |
| Example 12 | 80 J/m$^2$ | 0.20 | Good | Good | Good |
| Example 13 | 100 J/m$^2$ | 0.20 | Good | Good | Good |
| Example 14 | 110 J/m$^2$ | 0.18 | Good | Good | Good |
| Example 15 | 120 J/m$^2$ | 0.20 | Good | Good | Good |
| Example 16 | 90 J/m$^2$ | 0.18 | Good | Good | Good |
| Example 17 | 100 J/m$^2$ | 0.19 | Good | Good | Good |
| Example 18 | 50 J/m$^2$ | 0.17 | Good | Good | Good |
| Example 19 | 2 × 10$^{-2}$ C/m$^2$ | 0.17 | Good | Good | Good |
| Example 20 | 3 × 10$^{-2}$ C/m$^2$ | 0.17 | Good | Good | Good |
| Example 21 | 3 × 10$^{-2}$ C/m$^2$ | 0.18 | Good | Good | Good |
| Comparative Example 1 | 340 J/m$^2$ | 0.22 | Good | Good | Good |
| Comparative Example 2 | 100 J/m$^2$ | 0.22 | Bad | Good | Good |

The radiation-sensitive resin composition (1) of the present invention is non-sublimable and very useful as a sensitizing component of a chemically amplified resist which is sensitive to active rays such as deep ultraviolet rays represented, for example, by a KrF excimer laser (wavelength 248 nm), ArF excimer laser (wavelength: 193 nm), and F$_2$ excimer laser (wavelength: 157 nm). The chemically amplified radiation-sensitive resin composition containing the carbazole derivative (1) of the present invention can be used as a chemically amplified resist, which particularly exhibits high sensitivity without losing basic properties as a resist such as resolution and pattern profile. The composition also exhibits superior environmental resistance such as PED stability and excellent storage stability.

Obviously, numerous modifications and variations of the present invention are possible in light of the above teachings. It is therefore to be understood that, within the scope of the appended claims, the invention may be practiced otherwise than as specifically described herein.

What is claimed is:

1. A carbazole derivative of the following formula (1),

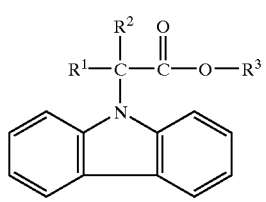

(1)

wherein R$^1$ and R$^2$ in the formula (1) independently represent a linear, branched, or cyclic alkyl group having 1–12 carbon atoms, an aromatic hydrocarbon group having 6–20 carbon atoms, an oxygen-containing organic group, or a nitrogen-containing organic group, and wherein R$^3$ represents a hydrogen atom or a monovalent organic group.

2. A carbazole derivative of the following formula (1),

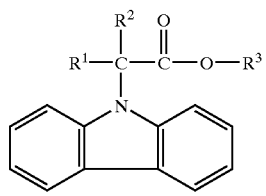

(1)

wherein $R^1$ and $R^2$ individually represent a hydrogen atom or a monovalent organic group, or $R^1$ and $R^2$ form, together with the carbon atom to which $R^1$ and $R^2$ bond, a divalent organic group having a 3–8 member carbocyclic structure or a 3–8 member heterocyclic structure, and wherein $R^3$ in the formula (1) is an i-propyl group, t-butyl group, or a cyclohexyl group.

3. The carbazole derivative according to claim 2, wherein the monovalent organic group represented by $R^1$ and $R^2$ in the formula (1) is a hydrogen atom, methyl group, ethyl group, n-propyl group, i-propyl group, n-butyl group, 2-methylpropyl group, 1-methylpropyl group, t-butyl group, phenyl group, or benzyl group, or a divalent organic group having an alicyclic ring formed by $R^1$, $R^2$, and the carbon atom to which $R^1$ and $R^2$ bond, which is derived fir cyclohexane.

4. The carbazole derivative according to claim 1, wherein the monovalent organic group represented by $R^3$ in the formula (1) is a linear, branched, or cyclic alkyl group having 1–12 carbon atoms, aromatic hydrocarbon group having 6–20 carbon atoms, oxygen-containing organic group, nitrogen-containing organic group, or acid-dissociable organic group.

5. The carbazole derivative according to claim 1, wherein the monovalent organic group represented by $R^3$ in the formula (1) is a hydrogen atom, methyl group, ethyl group, n-propyl group, n-butyl group, 2-methylpropyl group, or phenyl group, or an acid-dissociable organic groups selected from the group consisting of an i-propyl group, 1-methylpropyl group, t-butyl group, cyclohexyl group, benzyl group, t-butoxycarbonylmethyl group, 1-methoxyethyl group, 1-ethoxyethyl group, trimethylsilyl group, t-butoxycarbonyl group, tetrahydrofuranyl group, tetrahydropyranyl group, tetrahydrothiofuranyl group, and tetrahydrothiopyranyl group.

6. The carbazole derivative according to claim 2, wherein $R^1$ and $R^2$ in the formula (1) are hydrogen atoms.

7. A carbazole derivative, of the following formula (1),

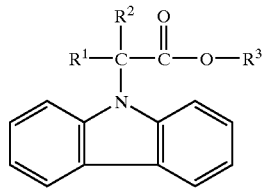

(1)

wherein $R^1$ and $R^2$ individually represent a hydrogen atom or a monovalent organic group, or $R^1$ and $R^2$ form, together with the carbon atom to which $R^1$ and $R^2$ bond, a divalent organic group having a 3–8 member carbocyclic structure or a 3–8 member heteroyclic structure, and wherein $R^3$ in the formula (1) is an acid dissociable organic group.

8. A chemically amplified radiation-sensitive resin composition comprising a carbazole derivative of the following formula (1),

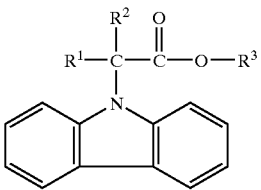

(1)

wherein $R^1$ and $R^2$ individually represent a hydrogen atom or a monovalent organic group, or $R^1$ and $R^2$ form, together with the carbon atom to which $R^1$ and $R^2$ bond, a divalent organic group having a 3–8 member carbocyclic structure or a 3–8 member heterocyclic structure, and $R^3$ represents a hydrogen atom or a monovalent organic group.

9. A positive tone radiation-sensitive resin composition comprising (A) a carbazole derivative of the following formula (1),

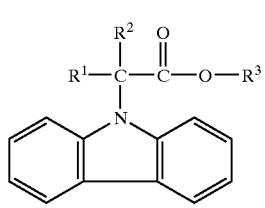

(1)

wherein $R^1$ and $R^2$ individually represent a hydrogen atom or a monovalent organic group, or $R^1$ and $R^2$ form, together with the carbon atom to which $R^1$ and $R^2$ bond, a divalent organic group having a 3–8 member carbocyclic structure or a 3–8 member heterocyclic structure, and $R^3$ represents a hydrogen atom or a monovalent organic group, (B) an acid-dissociable group-containing resin which is insoluble or scarcely soluble in alkali, but becomes alkali soluble when the acid-dissociable group dissociates, and (C) a photoacid generator.

10. The positive tone radiation-sensitive resin composition according to claim 9, comprising the carbazole derivative (A) in an amount of 0.1–40 parts by weight for 100 parts by weight of the acid-dissociable group-containing resin (B).

11. The positive tone radiation-sensitive resin composition according to claim 9, wherein the acid-dissociable group-containing resin (B) is a resin obtainable from a poly(p-hydroxystyrene), a copolymer of p-hydroxystyrene and p-hydroxy-α-methylstyrene, a copolymer of p-hydroxystyrene and styrene, or a copolymer of p-hydroxy styrene and/or p-hydroxy-α-methylstyrene and (meth) acrylic acid by replacing a part or all of the hydrogen atoms in the phenolic hydroxyl groups or the hydrogen atoms in the carboxylic groups with an acid-dissociable group.

12. The positive tone radiation-sensitive resin composition according to claim 9, wherein the acid-dissociable group is a substituted methyl group, 1-substituted ethyl group, 1-branched alkyl group, silyl group, germyl group, alkoxycarbonyl group, acyl group, or cyclic acid-decomposable group.

13. The positive tone radiation-sensitive resin composition according to claim 9, wherein the amount of the acid-dissociable groups introduced into the acid-dissociable group-containing resin (B) is 15–100%.

14. The positive tone radiation-sensitive resin composition according to claim 9, wherein the photoacid generator (C) is at least one compound selected from the group consisting of onium salt compounds, sulfone compounds, sulfonate compounds, sulfonimide compounds, disulfonyldiazomethane compounds, disulfonylmethane compounds, oximesulfonate compounds, and hydrazine sulfonate compounds.

15. The positive tone radiation-sensitive resin composition according to claim 9, comprising the photoacid genrator (C) in an amount of 0.1–20 parts by weight for 100 parts by weight of the acid-dissociable group-containing resin (B).

16. The positive tone radiation-sensitive resin composition according to claim 9, further comprising an acid diffusion controller.

17. The positive tone radiation-sensitive resin composition according to claim 16, wherein the acid diffusion controller is a nitrogen-containing organic compound.

18. A carbazole derivative of the following formula (1),

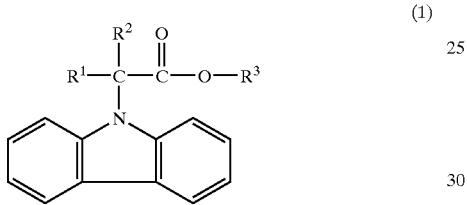

(1)

wherein $R^1$ and $R^2$ individually represent a hydrogen atom or a monovalent organic group with the proviso that either of $R^1$ or $R^2$ is an ethyl group, and $R^3$ represents a hydrogen atom or a monovalent organic group.

19. A carbazole derivative of the following formula (1),

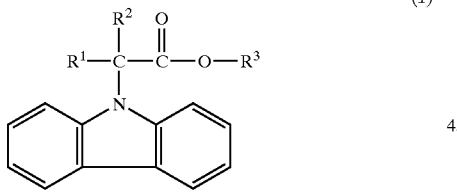

(1)

wherein $R^1$ and $R^2$ individually represent a hydrogen atom or a monovalent organic group with the proviso that either of $R^1$ or $R^2$ is a phenyl group, and $R^3$ in the formula (1) is a linear, branched, or cyclic alkyl group having 1–12 carbon atoms, an aromatic hydrocarbon group having 6–20 carbon atoms, an oxygen-containing organic group, a nitrogen-containing organic group, or an acid-dissociable organic group.

20. A carbazole derivative of the following formula (1),

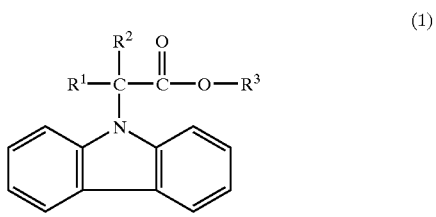

(1)

wherein $R^1$ represents a hydrogen atom or a monovalent organic group and $R^2$ represents a monovalent organic group, or $R^1$ and $R^2$ form, together with the carbon atom to which $R^1$ and $R^2$ bond, a divalent organic group having a 3–8 member carbocyclic structure or a 3–8 member heterocyclic structure with the proviso that when $R^1$ represents a hydrogen atom, $R^2$ is selected from the group consisting of an ethyl group, an n-propyl group, an i-propyl group, an n-butyl group, a 2-methylpropyl group, a 1-methylpropyl group, a t-butyl group, a phenyl group, and a benzyl group, and wherein $R^3$ in the formula (1) is an i-propyl group, t-butyl group, cyclohexyl group, or benzyl group.

21. The carbazole derivative according to claim 20, wherein $R^1$ and $R^2$ in formula (1) are each independently represented by a monovalent organic group selected from the group consisting of a methyl group, an ethyl group, an n-propyl group, an i-propyl group, an n-butyl group, a 2-methylpropyl group, a 1-methylpropyl group, a t-butyl group, a phenyl group, and a benzyl group.

22. The carbazole derivative according to claim 20, wherein $R^1$ and $R^2$ in the formula (1) and the carbon atom to which $R^1$ and $R^2$ bond are part of a 6 member alicyclic ring.

* * * * *

UNITED STATES PATENT AND TRADEMARK OFFICE
CERTIFICATE OF CORRECTION

PATENT NO.    : 6,846,607 B2
DATED         : January 25, 2005
INVENTOR(S)   : Tomoki Nagai et al.

It is certified that error appears in the above-identified patent and that said Letters Patent is hereby corrected as shown below:

Column 45,
Line 27, "derived fir" should read -- derived from --.
Line 65, "heteroyclic" should read -- heterocyclic --.

Column 47,
Line 12, "genrator" should read -- generator --.

Column 48,
Line 38, "in formula" should read -- in the formula --.

Signed and Sealed this

Tenth Day of May, 2005

JON W. DUDAS
*Director of the United States Patent and Trademark Office*